United States Patent
Kley et al.

(10) Patent No.: US 9,126,985 B2
(45) Date of Patent: *Sep. 8, 2015

(54) TETRA- AND PENTASUBSTITUTED BENZIMIDAZOLIUM COMPOUNDS

(71) Applicants: Joerg Kley, Mittelbiberach (DE); Sara Frattini, Castelleone (IT); Dieter Hamprecht, Pozzolengo (IT)

(72) Inventors: Joerg Kley, Mittelbiberach (DE); Sara Frattini, Castelleone (IT); Dieter Hamprecht, Pozzolengo (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/330,021

(22) Filed: Jul. 14, 2014

(65) Prior Publication Data

US 2015/0018315 A1    Jan. 15, 2015

(30) Foreign Application Priority Data

Jul. 15, 2013 (EP) .................................... 13176480

(51) Int. Cl.
| | |
|---|---|
| *A61K 31/497* | (2006.01) |
| *C07D 401/14* | (2006.01) |
| *C07D 403/12* | (2006.01) |
| *C07D 405/14* | (2006.01) |
| *A61K 31/675* | (2006.01) |
| *A61K 45/06* | (2006.01) |
| *C07F 9/572* | (2006.01) |
| *C07F 9/6558* | (2006.01) |
| *C07F 9/40* | (2006.01) |

(52) U.S. Cl.
CPC ............ *C07D 405/14* (2013.01); *A61K 31/497* (2013.01); *A61K 31/675* (2013.01); *A61K 45/06* (2013.01); *C07D 401/14* (2013.01); *C07D 403/12* (2013.01); *C07F 9/4006* (2013.01); *C07F 9/5728* (2013.01); *C07F 9/65583* (2013.01)

(58) Field of Classification Search
CPC ... C07D 401/14; C07D 403/12; C07D 405/14
See application file for complete search history.

(56) References Cited

U.S. PATENT DOCUMENTS 5,250,527 A    10/1993 Ife

FOREIGN PATENT DOCUMENTS

| WO | 03070182 | 8/2003 |
|---|---|---|
| WO | 2004073629 A2 | 9/2004 |
| WO | 2005018644 A1 | 3/2005 |
| WO | 2006022935 A1 | 3/2006 |
| WO | 2007018640 | 2/2007 |
| WO | 2011079087 | 6/2011 |

*Primary Examiner* — Brian McDowell
(74) *Attorney, Agent, or Firm* — Michael P. Morris; Edward S. Lazer

(57) ABSTRACT

The present invention relates to compounds of general formula (I)

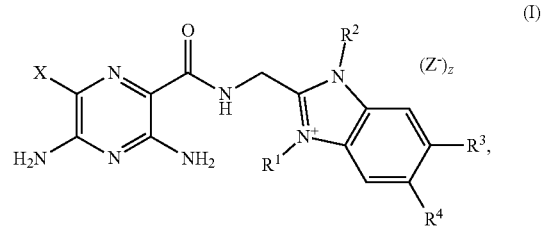

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

10 Claims, No Drawings

TETRA- AND PENTASUBSTITUTED BENZIMIDAZOLIUM COMPOUNDS

1. FIELD OF THE INVENTION

The present invention relates to compounds of general formula (I)

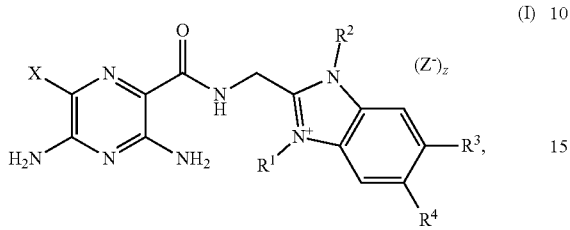

and the tautomers and the salts thereof, particularly the pharmaceutically acceptable salts thereof with inorganic or organic acids including zwitterions, which have valuable pharmacological properties, particularly an inhibitory effect on epithelial sodium channels, the use thereof for the treatment of diseases, particularly diseases of the lungs and airways.

2. BACKGROUND TO THE INVENTION

WO2011079087 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways. The new compounds of the present invention exhibit a reduced permeability being beneficial for topical lung treatment.

3. DETAILED DESCRIPTION OF THE INVENTION

It has surprisingly been found that the problem mentioned above is solved by compounds of formula (I) of the present invention.

The present invention therefore relates to a compound of formula (I),

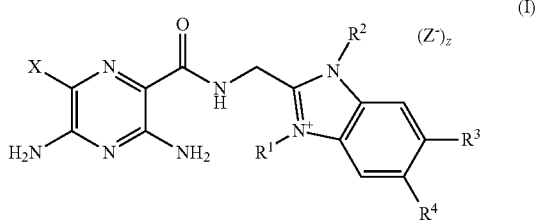

wherein
X denotes Cl or Br,
$R^1$ denotes allyl-, NC—$C_{3-4}$-alkylene-, H—(O—$CH_2$—$CH_2$)$_q$—, $CH_3$—(O—$CH_2$—$CH_2$)$_m$—, tetrahydropyranyl-($CH_2$)$_r$—, N—[$R^{11}$—(O—$CH_2$—$CH_2$)$_s$—$CH_2$—C(O)]-piperidin-4-yl-($CH_2$)$_r$— or $R^9R^{10}$N—C(O)-(2-oxo-2H-pyrid-1-yl)-$C_{3-5}$-alkylene-,
$R^2$ denotes $C_{1-3}$-alkyl-,
$R^3$ and $R^4$ denote independently H, halogen, HO—, (HO—$C_{2-3}$-alkylene)$_2$N—, ($R^7$O—)($R^8$O—)P(O)—($CH_2$)$_n$—O—, $R^5R^6$N—C(O)—$CH_2$—O—, HO—($CH_2$)$_2$—O—, ($CH_3$)$_2$P(O)—$CH_2$O— or a substituent of formula (bg)

and if $R^3$ denotes H or halogen, then $R^4$ does not denote H or halogen,
and if $R^4$ denotes H or halogen, then $R^3$ does not denote H or halogen,
$R^5$ and $R^6$ denote independently H, $C_{1-2}$-alkyl- or
$R^5$ and $R^6$ together with the nitrogen atom they are attached to form a 6-membered heterocycle from the group consisting of thiomorpholine, thiomorpholine-S-oxide, thiomorpholine-dioxide,
$R^7$ and $R^8$ denote independently H or $C_{1-3}$-alkyl-,
$R^9$ and $R^{10}$ denote independently H or $C_{1-3}$-alkyl-,
$R^{11}$ denotes H or $C_{1-3}$-alkyl-,
m denotes 2, 3 or 4,
n denotes 2 or 3,
q denotes 3 or 4,
r denotes 0, 1, 2 or 3,
s denotes 0, 1 or 2,
$Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate and p-toluenesulfonate,
z denotes 0 for negatively charged substituents $R^1$-$R^4$, 1 for uncharged substituents $R^1$-$R^4$ or 2 for positively charged substituents $R^1$-$R^4$,
and tautomers and optionally the pharmacologically acceptable acid addition salts thereof.

Preferred compounds of formula (I) are those wherein
$R^1$ denotes allyl-, NC—$C_{3-4}$-alkylene-, H—(O—$CH_2$—$CH_2$)$_q$—, tetrahydropyranyl-($CH_2$)$_{0-1}$—, N-acetyl-piperidinyl-, or $R^9R^{10}$N—C(O)-(2-oxo-2H-pyrid-1-yl)-$C_{3-5}$-alkylene-,
$R^9$ and $R^{19}$ denote independently H or methyl-,
q denotes 3 or 4.

Also preferred compounds of formula (I) are those wherein $R^2$ denotes $C_{1-3}$-alkyl-.

Also preferred compounds of formula (I) are those wherein
$R^3$ denotes H, HO—, (HO—$C_{2-3}$-alkylene)$_2$N—, ($R^7$O—)($R^8$O—)P(O)—($CH_2$)$_n$—O—, $R^5R^6$N—C(O)—$CH_2$—O— or HO—($CH_2$)$_2$—O—,
and if $R^3$ denotes H, then $R^4$ does not denote H or halogen,
$R^5$ and $R^6$ denote independently H or $C_{1-2}$-alkyl-,
$R^7$ and $R^8$ denote independently H or $C_{1-3}$-alkyl-,
n denotes 2 or 3.

Also preferred compounds of formula (I) are those wherein
$R^4$ denotes H, halogen or $R^5R^6$N—C(O)—$CH_2$—O—,
and if $R^4$ denotes H or halogen, then $R^3$ does not denote H,
$R^5$ and $R^6$ denote independently H or $C_{1-2}$-alkyl-.

Particularly preferred are compounds of formula (I) wherein

R¹ denotes a substituent selected from the group consisting of formula (aa)-(ag)

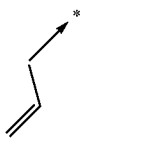
(aa)

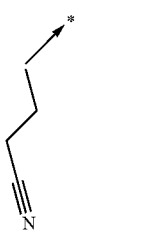
(ab)

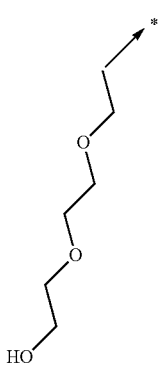
(ac)

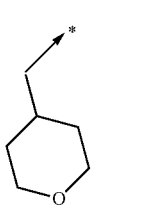
(ad)

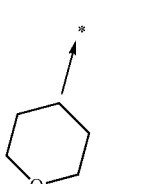
(ae)

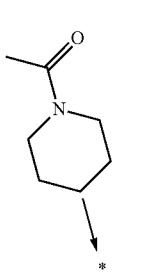
(af)

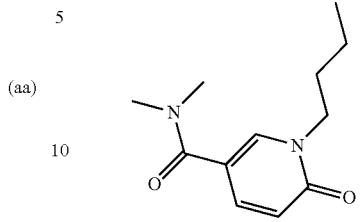
(ag)

Also particularly preferred are compounds of formula (I) wherein

R² denotes ethyl-.

Also particularly preferred are compounds of formula (I) wherein

R³ denotes H, HO— or

R³ denotes a substituent selected from the group consisting of formula (ba)-(bf)

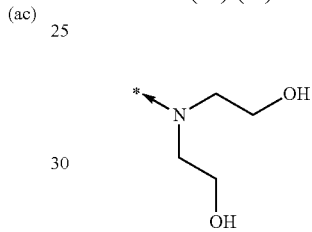
(ba)

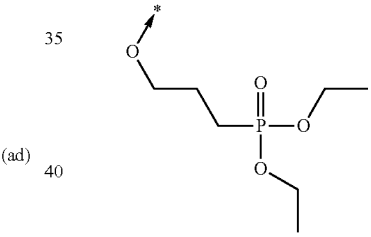
(bb)

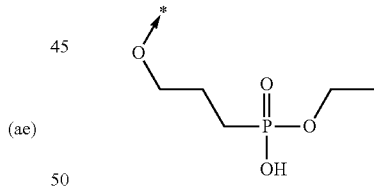
(bc)

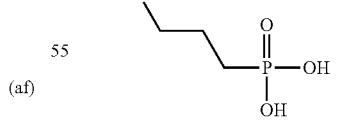
(bd)

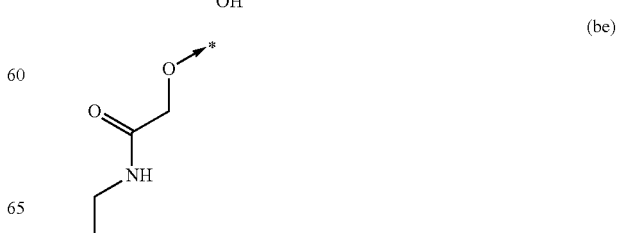
(be)

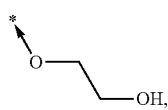
(bf)

and if R³ denotes H, then R⁴ does not denote H or Cl.

Also particularly preferred are compounds of formula (I) wherein

R⁴ denotes H, Cl or a substituent of formula (ca)

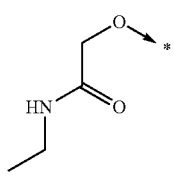
(ca)

and if R⁴ denotes H or Cl, then R³ does not denote H.

Especially preferred are compounds of formula (I)

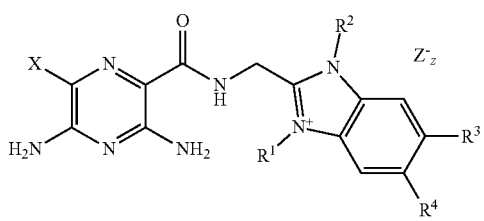
(I)

wherein

X denotes Cl or Br,

R¹ denotes a substituent selected from the group consisting of formula (aa)-(ag)

(aa)

(ab)

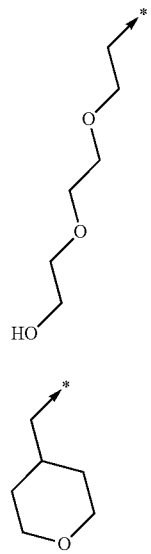
(ac)

(ad)

(ae)

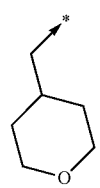
(af)

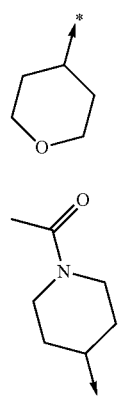

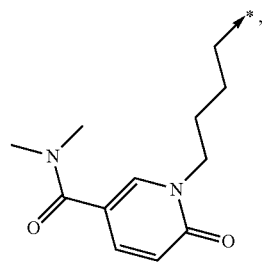
(ag)

R² denotes ethyl-,

R³ denotes H, HO— or

R³ denotes a substituent selected from the group consisting of formula (ba)-(bf)

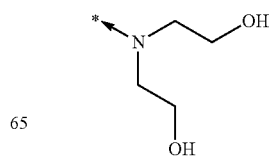
(ba)

-continued (bb)
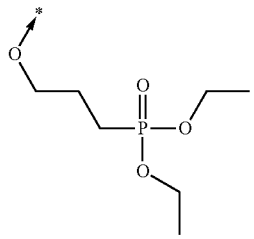

(bc)
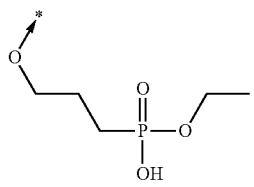

(bd)
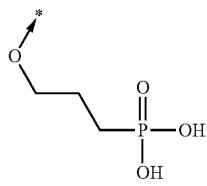

(be)
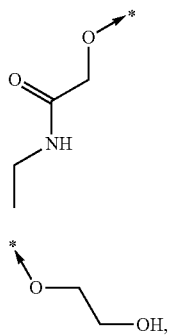

(bf)
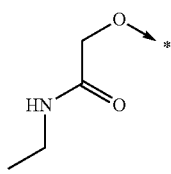

and if $R^3$ denotes H, then $R^4$ does not denote H or Cl, $R^4$ denotes H, Cl or a substituent of formula (ca)

(ca)

and if $R^4$ denotes H or Cl, then $R^3$ does not denote H, $Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate, p-toluenesulfonate, z denotes 0 for negatively charged substituents $R^1$-$R^4$, 1 for uncharged substituents $R^1$-$R^4$ or 2 for positively charged substituents $R^1$-$R^4$, and tautomers and optionally the pharmacologically acceptable acid addition salts thereof.

A further embodiment of the current invention is compounds of formula (I), or a pharmaceutically acceptable salt thereof for use as a medicament.

A further embodiment of the current invention is compounds of formula (I), or a pharmaceutically acceptable salt thereof for use in the treatment of a disease selected from among respiratory diseases or complaints and allergic diseases of the airways.

Preferred are compounds of formula (I) or a pharmaceutically acceptable salt thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins, preferably chronic bronchitis, acute bronchitis, bronchitis, chronic obstructive bronchitis (COPD), asthma (intrinsic or allergic), cystic fibrosis and pediatric asthma, preferably chronic bronchitis, COPD and cystic fibrosis.

A further embodiment of the current invention is a pharmaceutical composition comprising at least one compound according to the invention or a pharmaceutically acceptable salt thereof and a pharmaceutically acceptable carrier.

A further embodiment of the current invention are medicament combinations which contain, besides one or more compounds of a compound according to the invention, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof, preferably VX-770 and VX-809, or double or triple combinations thereof.

4. TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal bond indicates the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

If a compound of the present invention is depicted in the form of a chemical name and as a formula, in case of any discrepancy the formula shall prevail. An asterisk is may be used in sub-formulas to indicate the bond which is connected to the core molecule as defined.

For example, the term "3-carboxypropyl-group" represents the following substituent:

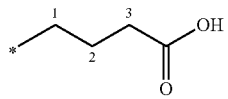

wherein the carboxy group is attached to the third carbon atom of the propyl group.

The terms "1-methylpropyl-", "2,2-dimethylpropyl-" or "cyclopropylmethyl-" group represent the following groups:

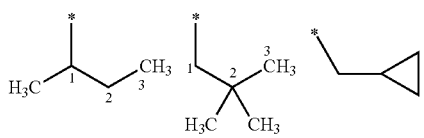

The asterisk may be used in sub-formulas to indicate the bond which is connected to the core molecule as defined.

Likewise an arrow together with an asterisk may be used in sub-formulas to indicate the bond which is connected to the core molecule as defined.

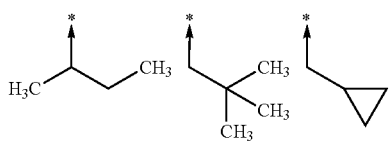

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethane-sulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

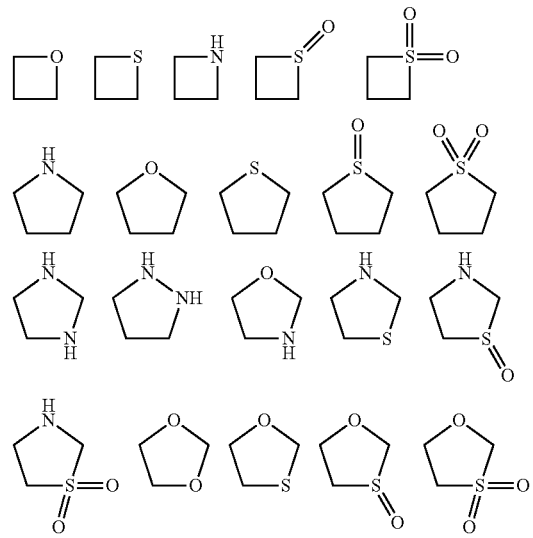

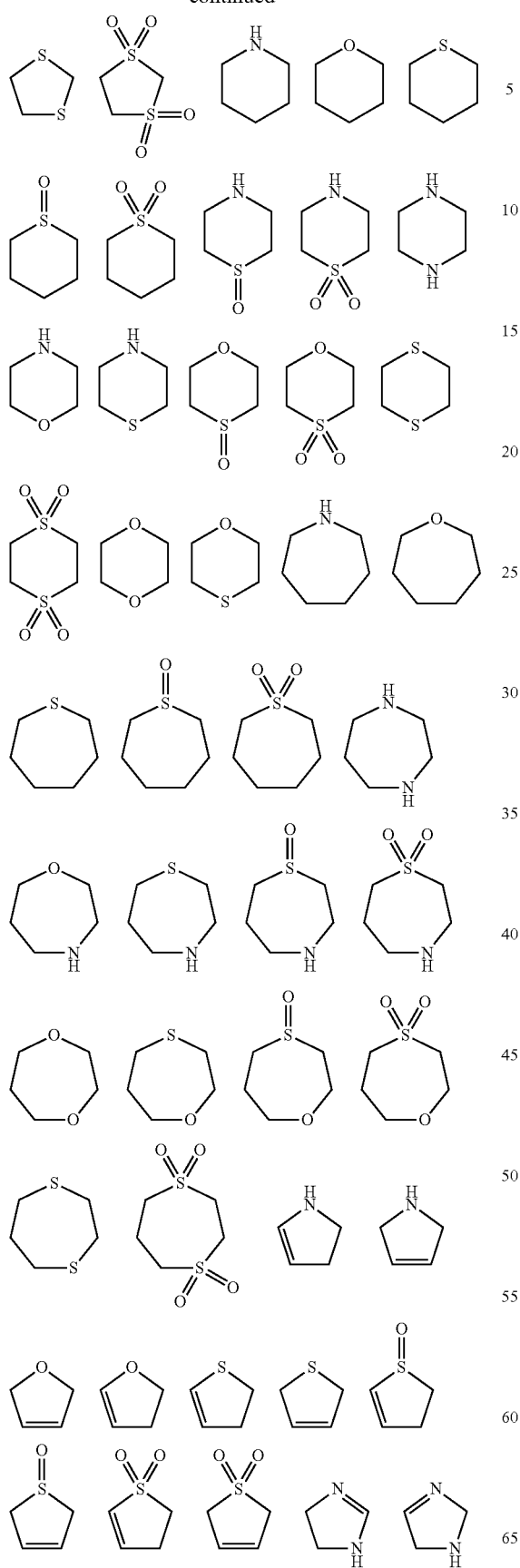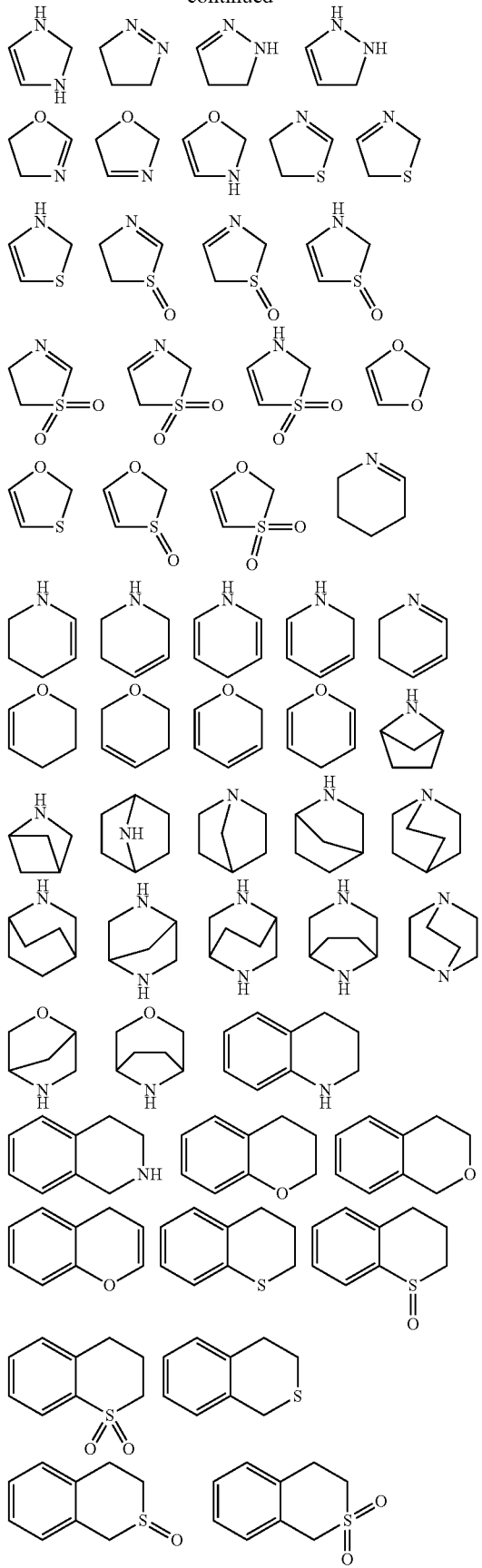

-continued

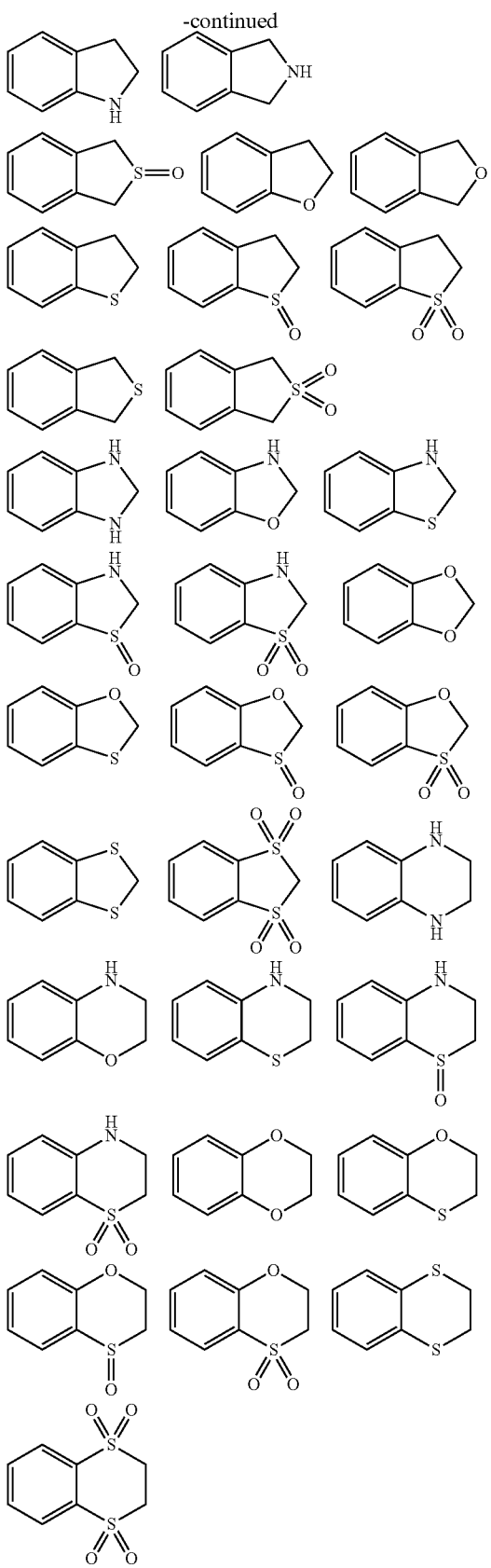

The term heteroaromatic means heteroaryl, monocyclic $C_{5-14}$-heteroaryl, or polycyclic $C_{5-14}$-heteroaryl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

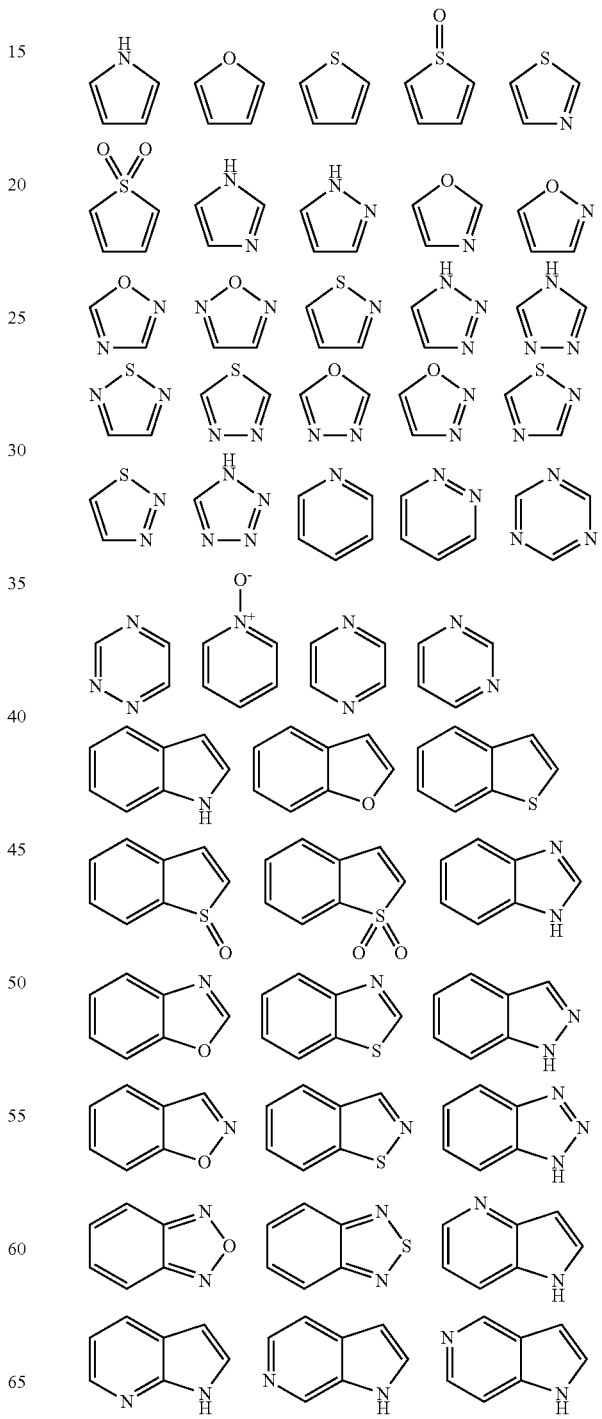

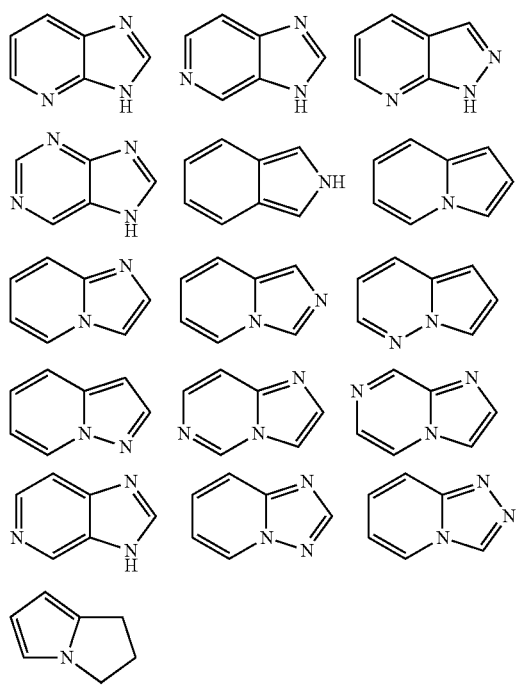

The term "monocyclic $C_{5-7}$-heterocyclyl" means a saturated or unsaturated non-aromatic monocyclic-ring systems containing one or more heteroatoms selected from N, O or $S(O)_r$, wherein r=0, 1 or 2, consisting of 5 to 7 ring atoms. The term "monocyclic $C_{5-7}$-heterocyclyl" is intended to include all the possible isomeric forms.

Thus, the term "monocyclic $C_{5-7}$-heterocyclyl" includes the following exemplary structures which are not depicted as radicals as each form may be attached through a covalent bond to any atom so long as appropriate valences are maintained:

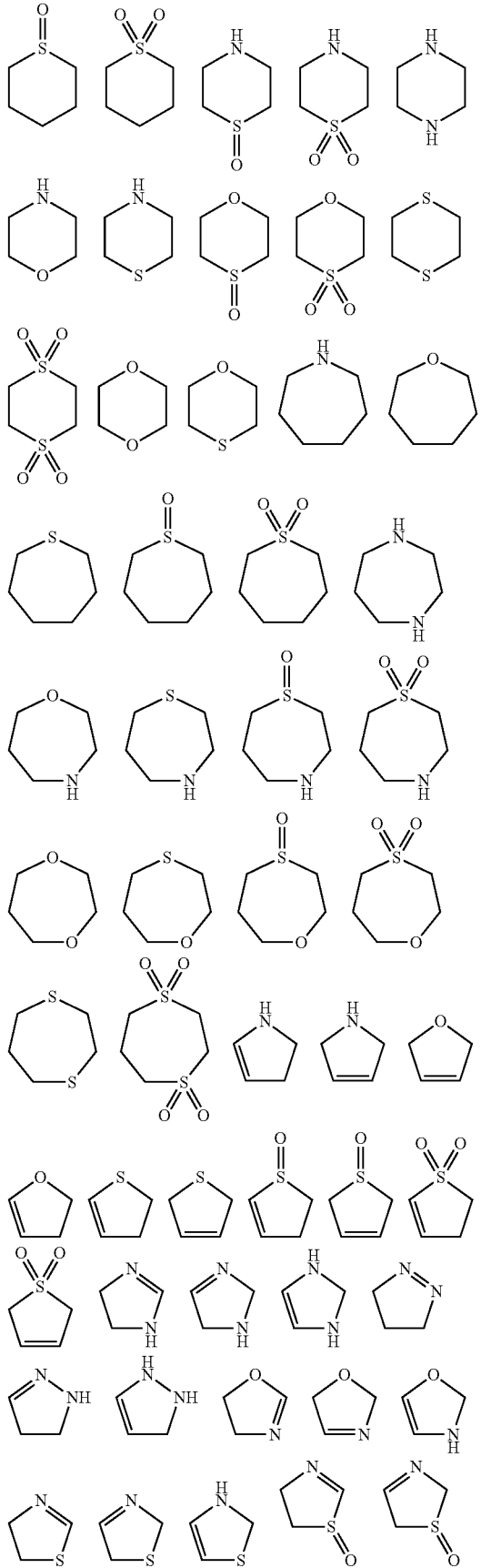

-continued

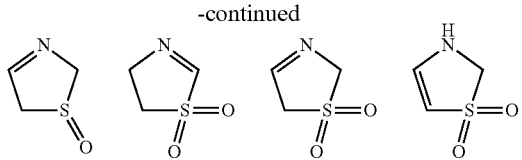

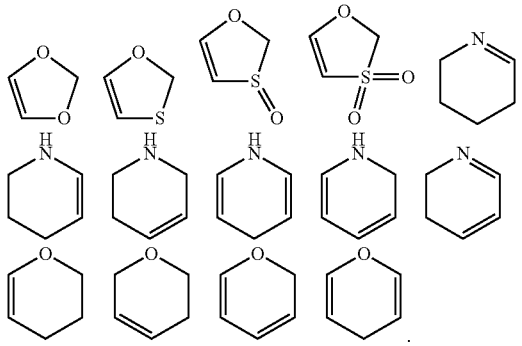

The term "monocyclic $C_{5-6}$-heteroaryl" means a monocyclic-ring systems containing one or more heteroatoms selected from N, O or $S(O)_r$, wherein r=0, 1 or 2, consisting of 5 or 6 ring atoms wherein at least one of the heteroatoms is part of aromatic ring. The term "monocyclic $C_{5-6}$-heteroaryl" is intended to include all the possible isomeric forms.

Thus, the term "monocyclic $C_{5-6}$-heteroaryl" includes the following exemplary structures which are not depicted as radicals as each form may be attached through a covalent bond to any atom so long as appropriate valences are maintained:

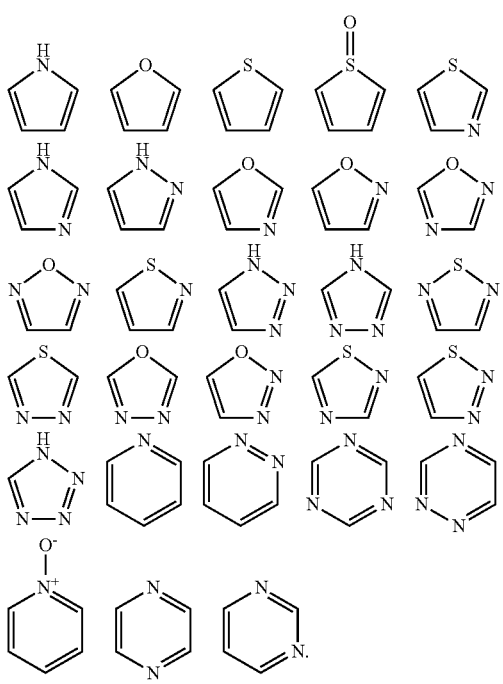

The term "bicyclic $C_{8-10}$-heterocyclyl" means a saturated or unsaturated bicyclic-ring systems including aromatic ring systems containing one or more heteroatoms selected from N, O or $S(O)_r$, wherein r=0, 1 or 2, consisting of 8 to 10 ring atoms wherein the heteroatoms is optionally part of the aromatic ring. The term "bicyclic $C_{8-10}$-heterocyclyl" is intended to include all the possible isomeric forms.

Thus, the term "bicyclic $C_{8-10}$-heterocyclyl" includes the following exemplary structures which are not depicted as radicals as each form may be attached through a covalent bond to any atom so long as appropriate valences are maintained:

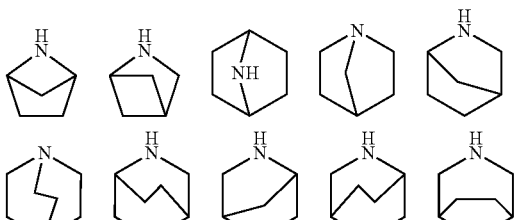

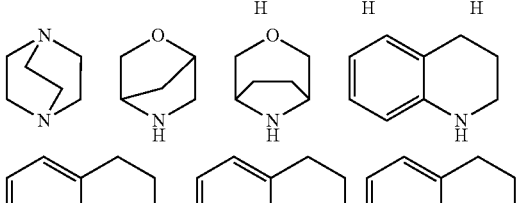

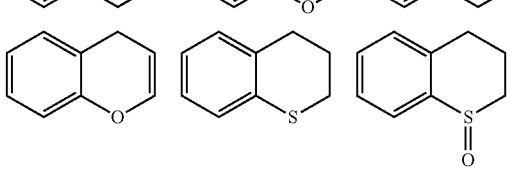

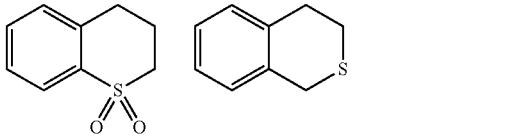

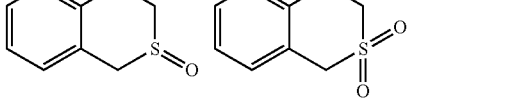

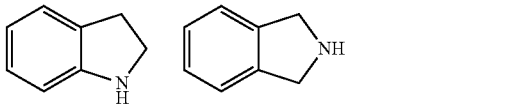

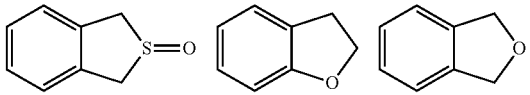

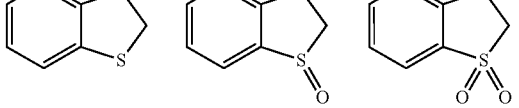

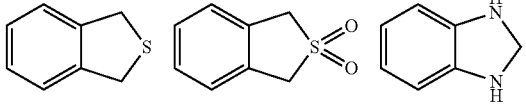

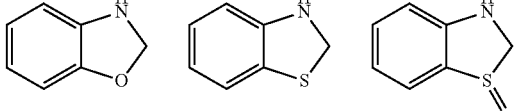

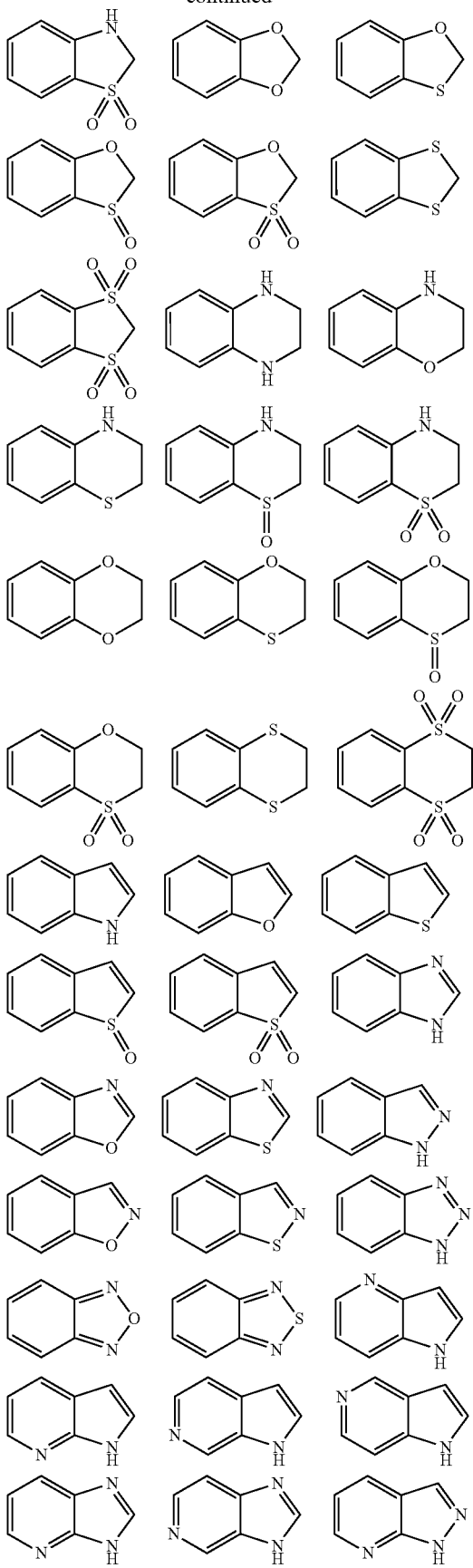
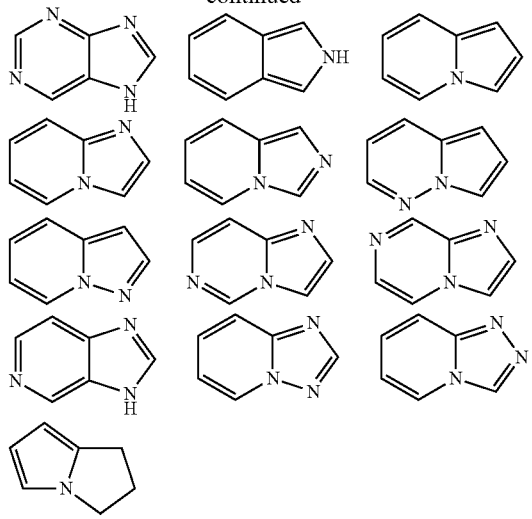

The term "annelated species of aryl or heterocyclyl" as used herein, either alone or in combination with another substituent wherein the annelated species presents as an arylhet (a), a het-aryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —CH($CH_3$)—, —$CH_2$—$CH_2$—$CH_2$—, —C($CH_3$)$_2$—, —CH($CH_2CH_3$)—, —CH($CH_3$)—$CH_2$—, —$CH_2$—CH($CH_3$)—, —$CH_2$—$CH_2$—$CH_2$—$CH_2$—, —$CH_2$—$CH_2$—CH($CH_3$)—, —CH($CH_3$)—$CH_2$—$CH_2$—, —$CH_2$—CH($CH_3$)—$CH_2$—, —CH($CH_3$)—$CH_2$—, —$CH_2$—C($CH_3$)$_2$—, —C($CH_3$)$_2$—$CH_2$—, —CH($CH_3$)—CH($CH_3$)—, —$CH_2$—CH($CH_2CH_3$)—, —CH($CH_2CH_3$)—$CH_2$—, —CH($CH_2CH_2CH_3$)—, —CH(CH($CH_3$))$_2$— and —C($CH_3$)($CH_2CH_3$)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkenylene" is used for a group as defined in the definition for "$C_{1-n}$-alkylene" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{2-n}$-alkynylene" is used for a group as defined in the definition for "$C_{1-n}$-alkylene" with at least two carbon atoms, if at least two of those carbon atoms of said group are bonded to each other by a triple bond.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

In all cases of contradictions between structure and their naming, structure shall prevail.

5. PREFERRED EMBODIMENTS

The substituent X denotes Cl or Br, preferably Cl.
The substituent $R^1$ denotes allyl-, NC—$C_{3-4}$-alkylene-, H—(O—$CH_2$—$CH_2$)$_q$—, $CH_3$—(O—$CH_2$—$CH_2$)$_m$—, tetrahydropyranyl-($CH_2$)$_r$—, N—[$R^{11}$—(O—$CH_2$—$CH_2$)$_s$—$CH_2$—C(O)]-piperidin-4-yl-($CH_2$)$_r$— or $R^9R^{10}$N—C(O)-(2-oxo-2H-pyrid-1-yl)-$C_{3-5}$-alkylene-, preferably allyl-, NC—$C_{3-4}$-alkylene-, H—(O—$CH_2$—$CH_2$)$_q$—, tetrahydropyranyl-($CH_2$)$_{0-1}$—, N-acetyl-piperidinyl-, or $R^9R^{10}$N—C(O)-(2-oxo-2H-pyrid-1-yl)-$C_{3-5}$-alkylene-, particularly preferred is a substituent selected from the group consisting of formula (aa)-(ag)

(aa)

(ab)

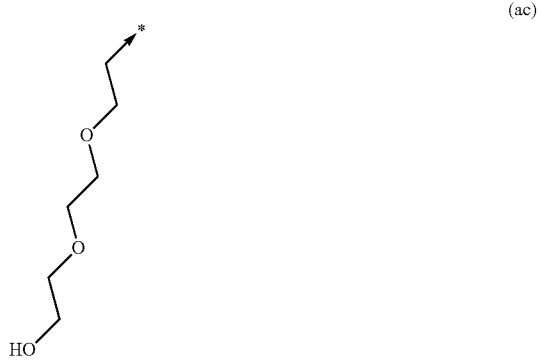

(ac)

(ad)

(ae)

(af)

-continued (ag)
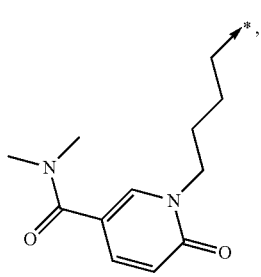

also particularly preferred is a substituent selected from the group consisting of formula (ab)-(af)

(ab)
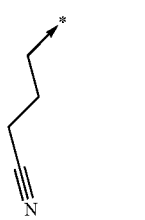

(ac)
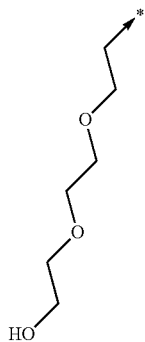

(ad)
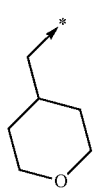

(ae)
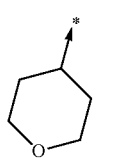

(af)
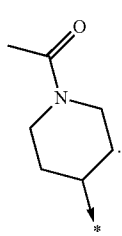

The substituent $R^2$ denotes $C_{1-3}$-alkyl-, preferably ethyl-.

The substituent $R^3$ denotes H, halogen, HO—, (HO—$C_{2-3}$-alkylene)$_2$N—, ($R^7$O—)($R^8$O—)P(O)—(CH$_2$)$_n$—O—, $R^5R^6$N—C(O)—CH$_2$—O—, HO—(CH$_2$)$_2$—O—, (CH$_3$)$_2$P(O)—CH$_2$O— or a substituent of formula (bg)

(bg)
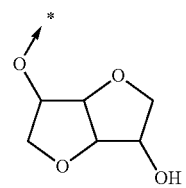

and if $R^3$ denotes H or halogen, then $R^4$ does not denote H or halogen; preferably H, HO—, (HO—$C_{2-3}$-alkylene)$_2$N—, ($R^7$O—)($R^8$O—)P(O)—(CH$_2$)$_n$—O—, $R^5R^6$N—C(O)—CH$_2$—O— or HO—(CH$_2$)$_2$—O—, and if $R^3$ denotes H, then $R^4$ does not denote H or halogen; particularly preferred is H, HO— or a substituent selected from the group consisting of formula (ba)-(bf)

(ba)
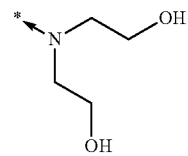

(bb)
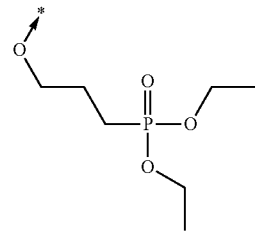

(bc)
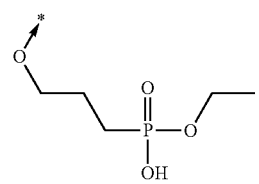

(bd)
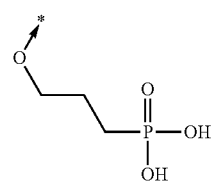

(be)
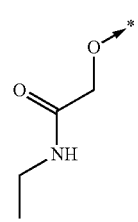

-continued

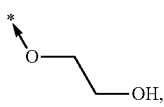
(bf)

and if $R^3$ denotes H, then $R^4$ does not denote H or Cl; also particularly preferred is HO— or a substituent selected from the group consisting of formula (ba), (be) or (bf)

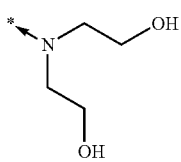
(ba)

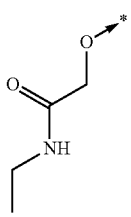
(be)

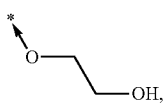
(bf)

also particularly preferred is a substituent selected from the group consisting of formula (bb)-(bd)

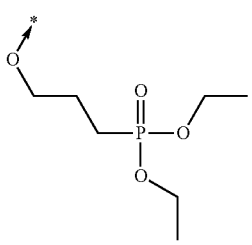
(bb)

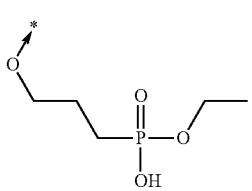
(bc)

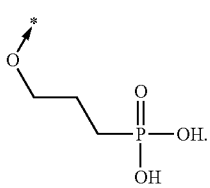
(bd)

The substituent $R^4$ denotes H, halogen, HO—, (HO—$C_{2-3}$-alkylene)$_2$N—, ($R^7$O—)($R^8$O—)P(O)—(CH$_2$)$_n$—O—, $R^5R^6$N—C(O)—CH$_2$—O—, HO—(CH$_2$)$_2$—O—, (CH$_3$)$_2$P(O)—CH$_2$O— or a substituent of formula (bg)

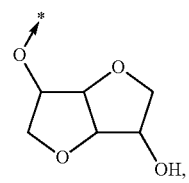
(bg)

and if $R^4$ denotes H or halogen, then $R^3$ does not denote H or halogen; preferably H, Cl or $R^5R^6$N—C(O)—CH$_2$—O—, and if $R^4$ denotes H or Cl, then $R^3$ does not denote H; particularly preferred H, Cl or a substituent of formula (ca)

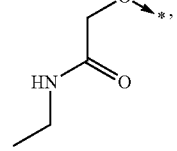
(ca)

and if $R^4$ denotes H or Cl, then $R^3$ does not denote H; also particularly preferred is Cl or a substituent of formula (ca)

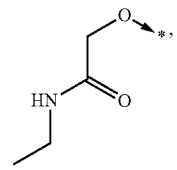
(ca)

and if $R^4$ denotes Cl, then $R^3$ does not denote H.

The substituent $R^5$ denotes H or $C_{1-2}$-alkyl-, preferably H or ethyl-.

The substituent $R^6$ denotes H or $C_{1-2}$-alkyl-, preferably H or ethyl-, or the substituents $R^5$, $R^6$ together with the nitrogen atom they are attached to form a 6-membered heterocycle from the group consisting of thiomorpholine, thiomorpholine-S-oxide, thiomorpholine-dioxide, The substituent $R^7$ denotes H or $C_{1-3}$-alkyl-, preferably H or ethyl-.

The substituent $R^8$ denotes H or $C_{1-3}$-alkyl-, preferably H or ethyl-, particularly preferred H.

The substituent $R^9$ denotes H or $C_{1-3}$-alkyl-, preferably H or methyl, particularly preferred methyl.

The substituent $R^{10}$ denotes H or $C_{1-3}$-alkyl-, preferably H or methyl, particularly preferred is methyl.

The substituent $R^{11}$ denotes H or $C_{1-3}$-alkyl-, preferably H.

Variable m denotes 2, 3 or 4, preferably 2 or 3, particularly preferred is 2.

Variable n denotes 2 or 3, preferably 3.
Variable q denotes 3 or 4, preferably 3.
Variable r denotes 0, 1, 2 or 3, preferably 0 or 1.
Variable s denotes 0, 1 or 2, preferably 0 or 1.
The anion $Z^-$ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate or p-toluenesulfonate, preferably chloride, formiate and trifluoroacetate.
Variable z denotes 0 for negatively charged substituents $R^1$-$R^4$, 1 for uncharged substituents $R^1$-$R^4$ or 2 for positively charged substituents $R^1$-$R^4$,
and tautomers and optionally the pharmacologically acceptable acid addition salts thereof.

Any and each other of the substituents defined above may be combined with each other.

6. PREPARATION

The following methods are suitable for preparing compounds of general formula (I).

The compounds according to the invention may be obtained using methods of synthesis which are known to one skilled in the art and described in the literature of organic synthesis. General methods for functional groups protection and deprotection steps are described e.g. in: Greene, T. W. and Wuts, P. G. M. (eds.): *Protective Groups in Organic Synthesis, third edition* 1999; John Wiley and Sons, Inc. Preferably the compounds are obtained analogously to the methods of preparation explained more fully hereinafter, in particular as described in the experimental section.

Compounds of general formula (I) can be prepared by standard amidation procedures from amines of general formula (II) and the appropriate 3,5-diaminopyrazine-2-carboxylic acid applying e.g. the coupling reagent HATU. Amines (II) can be prepared from N-protected precursors of general formula (III) by standard deprotection procedures. Suitable protecting groups in (III) are e.g. BOC (wherein $R^{PG}$ denotes NHPG with PG denoting tert-BuOC(O)—) and phthaloyl (wherein $R^{PG}$ denotes phthalimide). Compounds (III) can be prepared by alkylation of benzimidazoles of general formula (IIIa) applying alkylating agents $R^1$-LG. The leaving group LG can be e.g. Br or I.

Alternatively, compounds of general formula (I) can be prepared by alkylation of benzimidazoles of general formula (Ia) applying alkylating agents $R^1$-LG. The leaving group LG can be e.g. Br or I. Compounds of general formula (Ia) can be prepared by standard amidation procedures from amines of general formula (IIa) and the appropriate 3,5-diaminopyrazine-2-carboxylic acid applying e.g. the coupling reagent HATU. Amines (IIa) can be prepared from N-protected precursors of general formula (IIIa) by standard deprotection procedures. Suitable protecting groups in (IIIa) are e.g. BOC (wherein $R^{PG}$ denotes NHPG with PG denoting tert-BuOC(O)—) and phthaloyl (wherein $R^{PG}$ denotes phthalimide).

Benzimidazoles (IIIa) can be prepared from phenylenediamines (IV) in a two step procedure comprising (i) amidation with N-protected glycine using e.g. the coupling reagent TBTU and (ii) ring closure under acid catalysis, e.g. in glacial acetic acid at elevated temperature. Phenylenediamines can be prepared from the respective nitroanilins (V) by standard nitro reduction conditions (e.g. catalytic hydrogenation using raney-nickel as a catalyst). Compounds (V) can be prepared from derivatives (VI) by nucleophilic substitution of the leaving group LG (e.g. F or Cl) with a primary amine $R^2$—$NH_2$ as nucleophile. Alternatively, compounds (V) can be accessed from nitroanilines (Va) by either alkylation (using an alkylating agent $R^2$-LG) or reductive amination (using an appropriate aldehyde) of the aromatic amino group. Compounds (I), (Ia), (III), (IIIa) and (V) can be modified using methods of synthesis which are known to the one skilled in the art and described in the literature of organic synthesis, preferably by functional group protection or deprotection steps, esterifications, amidation, hydrogenations, or 1,3-dipolar cycloadditions. Thereby, before such a modification, the structures of $R^1$, $R^2$, $R^3$, and $R^4$ may be beyond of what is claimed hereinafter.

The skilled person will appreciate that within these general synthesis schemes, the substituents $R^1$ and $R^2$ can in principle be interchanged, meaning that $R^2$ instead of $R^1$ can be introduced in the late alkylation step applying an alkylating agent $R^2$-LG.

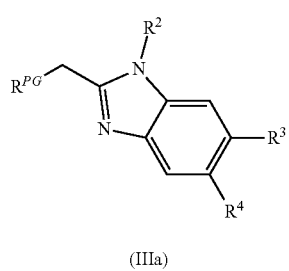

(IIIa)

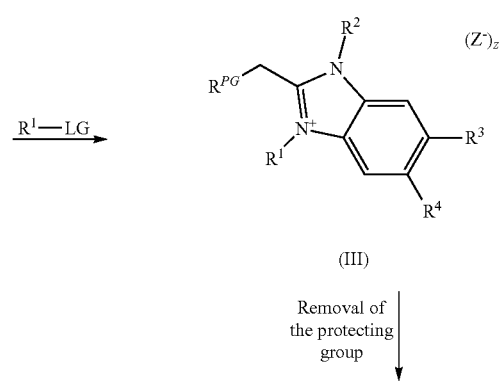

(III)

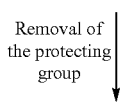

Removal of the protecting group

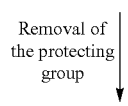

Removal of the protecting group

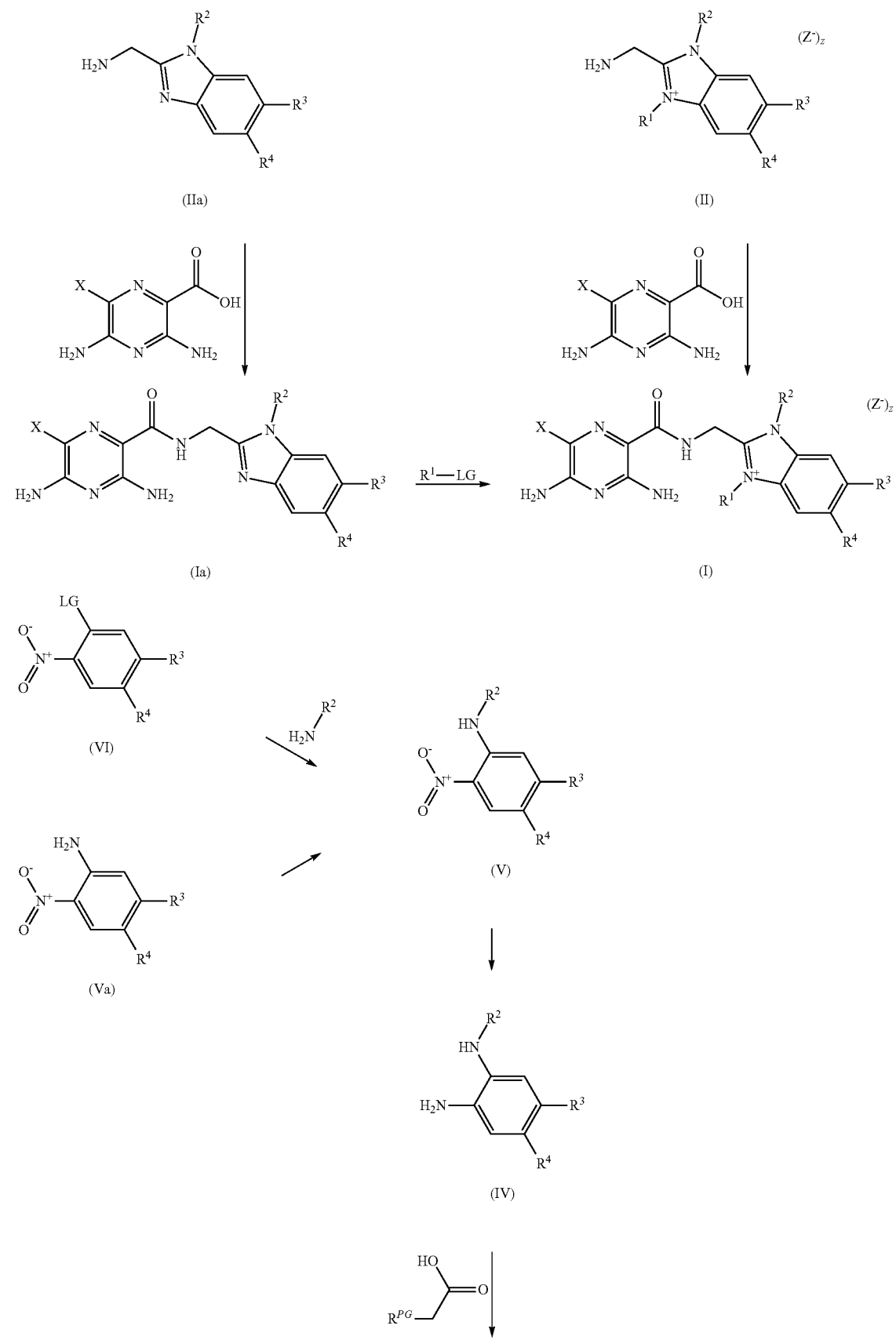

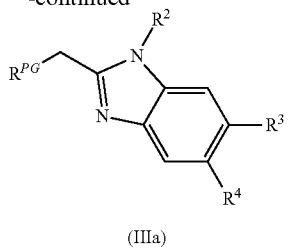

(IIIa)

7. EXAMPLES

Other features and advantages of the present invention will become apparent from the following more detailed Examples which illustrate, by way of example, the principles of the invention.

Where no salt forms of compounds are specified, the compound may exist as a free base or a salt or a zwitterion, depending on the chemical structure, the synthesis conditions and the processes of workup and purification applied. The skilled person will appreciate that the compound is not limited to a certain salt form. Where salt forms of compounds are specified, the stoichiometry of the counterion is usually omitted. In case of multiply charged counterions the skilled person will appreciate that the resulting salt form is uncharged, leading to the corresponding stoichiometry. The skilled person will appreciate that the compound is not limited to the mono salt form and that it may exist as a disalt, trisalt or other compound:counterion stoichiometries. Furthermore, the skilled person will appreciate that such compound may unexpectedly exist as a salt with a different counterion, depending on the synthesis conditions and the processes of workup and purification applied. Solely for the purpose of yield determination, an estimate of the nature of the counterion and of compound:counterion stoichiometry is made (as indicated by the formula given).

7.1 SYNTHESIS OF INTERMEDIATES

Intermediate A.1

3,5-Diamino-6-chloropyrazine-2-carboxylic acid

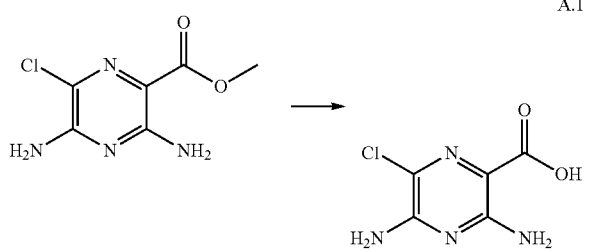

A mixture of methyl 3,5-diamino-6-chloropyrazine-2-carboxylate (100 g; 494 mmol), methanol (1 l) and NaOH (6 mol/l in water; 240 ml; 1.44 mol) is refluxed for 3 h. The mixture is allowed to cool to r.t. and then neutralized by addition of hydrochloric acid (6 mol/l in water; approx. 240 mL). Water (200 ml) is added. The precipitate formed is filtered off with suction, washed with water and dried at 60° C.

$C_5H_5ClN_4O_2$ ESI Mass spectrum: m/z=189 [M+H]+; m/z=187 [M−H]−

Intermediate A.2

3,5-Diamino-6-bromopyrazine-2-carboxylic acid

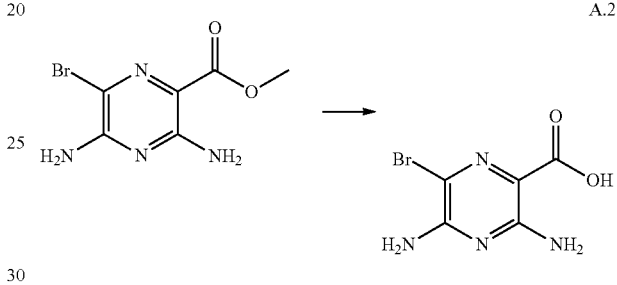

A.2 is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate A.1

Intermediate I.1

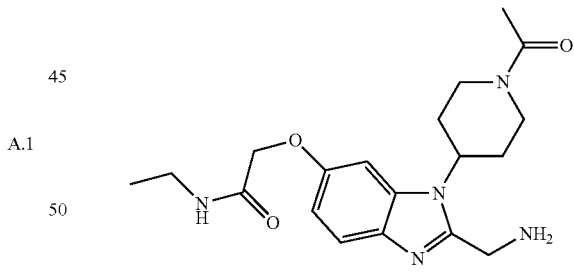

To a suspension of intermediate XVII.1 (0.82 g; 1.73 mmol) in dioxane (20 ml) is added hydrogen chloride (4.0 mol/L in dioxane; 4.33 ml; 17.3 mmol). The mixture is stirred over night and evaporated to dryness. The crude product is purified by cation exchange chromatography (SCX-2; 50 g; elution with methanolic ammonia) to yield the title compound.

$C_{19}H_{27}N_5O_3$ ESI Mass spectrum: m/z=375 [M+H]+

The following intermediates are prepared accordingly from the respective BOC-protected amines as indicated. Due to conditions applied, the syntheses may yield a free base, a TFA salt or other salt forms which can be applied equally to further synthesis steps.

| Example | Structure | BOC-protected amine applied | Synthesis comment |
|---|---|---|---|
| I.2 | 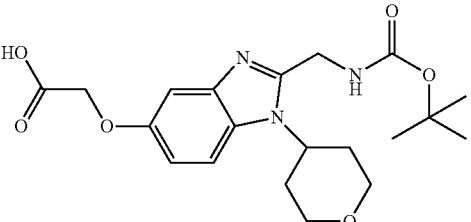 | XVII.2 | |
| I.3 | 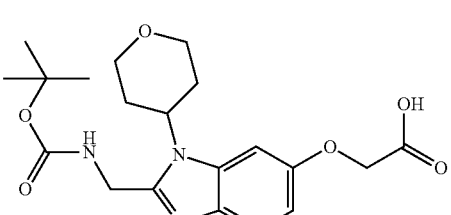 | XVII.3 | |

Intermediate II.1

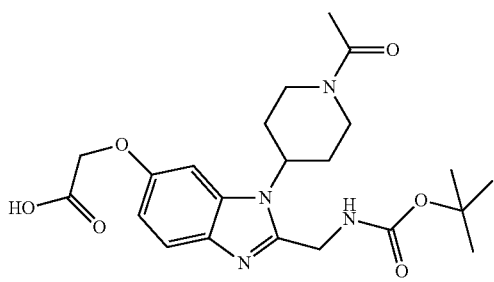

II.1

To a suspension of intermediate III.1 (9.20 g; 19.4 mmol) in THF (20 ml) and water (12 ml) is added sodium hydroxide (32% in water; 3.73 ml; 38.8 mmol). The mixture is stirred at r.t. for 1 h, then the organic solvent is evaporated. Citric acid is added to achieve pH 4. The mixture is extracted twice with DCM, the combined organic layers are dried with sodium sulphate and evaporated to dryness to yield the title compound.

$C_{22}H_{30}N_4O_6$ ESI Mass spectrum: m/z=447 [M+H]+

The following intermediates are prepared accordingly from the respective esters as indicated. Due to conditions applied, the syntheses may yield a free base, a TFA salt or other salt forms which can be applied equally to further synthesis steps.

| Example | Structure | ester applied | Synthesis comment |
|---|---|---|---|
| II.2 | 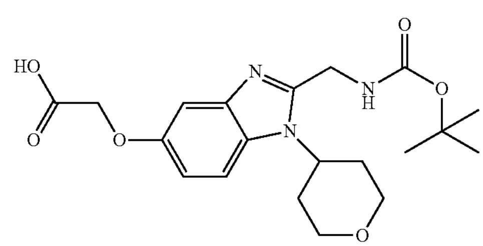 [SMILES: CC(C)(C)OC(=O)NCc1nc2cc(OCC(=O)O)ccc2n1C1CCOCC1] | III.2 | |
| II.3 | 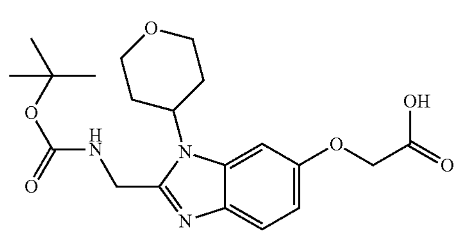 [SMILES: CC(C)(C)OC(=O)NCc1nc2ccc(OCC(=O)O)cc2n1C1CCOCC1] | III.3 | |

Intermediate III.1

Intermediate IV.1

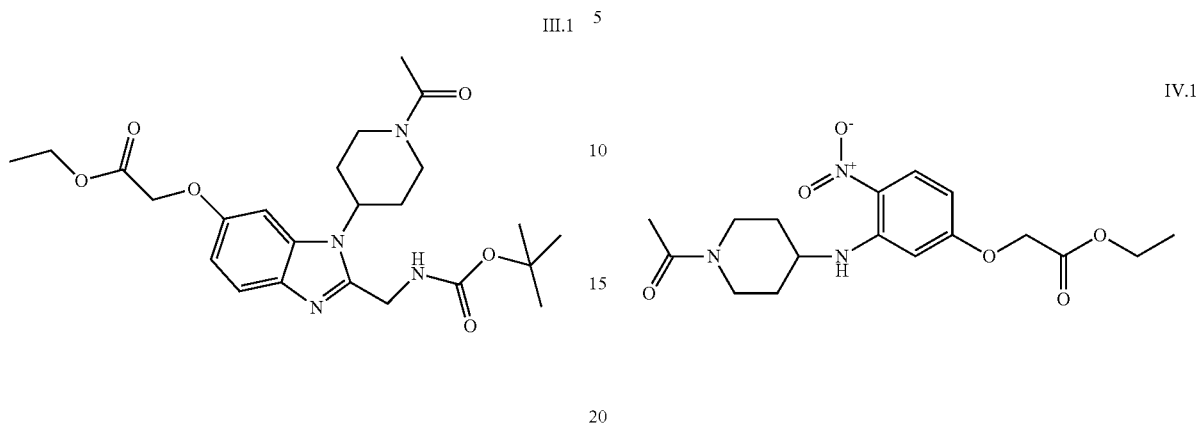

To a mixture of diamine intermediate V.1 (10.7 g; 29.7 mmol) in DMF (100 ml) and water (10 ml) is added dropwise acetic acid (2.67 ml; 44.5 mmol). A solution of tert-butyl-N-(2-oxoethyl)carbamate (4.72 g; 29.7 mmol) in DMF is added and the mixture is stirred at r.t. under air over night. Volatiles are evaporated and the residue is taken up in DCM and extracted with water. The organic layer is dried (sodium sulphate) and evaporated to dryness. The residue is triturated with ACN/water 2:8; the resulting solid is filtered off and dried in vacuo at 60° C. to yield the title compound.

$C_{24}H_{34}N_4O_6$ ESI Mass spectrum: m/z=475 [M+H]+

The following intermediates are prepared accordingly from the respective diamines as indicated. Due to conditions applied, the syntheses may yield a free base, a TFA salt or other salt forms which can be applied equally to further synthesis steps.

A mixture of aryl halide intermediate VII.2 (10.5 g; 41.9 mmol), the amine 1-acetyl-4-aminopiperidine hydrochloride (7.48 g; 41.9 mmol), potassium carbonate (20.3 g; 147 mmol) and DMF (60 ml) is stirred at r.t. for 2 days. The mixture is diluted with water and extracted with DCM. The organic layer is separated, dried and evaporated. The residue is purified by silica gel chromatography (cyclohexane/ethyl acetate 70:30→20:80) to yield the title compound.

$C_{17}H_{23}N_3O_6$ ESI Mass spectrum: m/z=366 [M+H]+

The following intermediates are prepared accordingly from the respective amines and the respective aryl halides as indicated. Due to conditions applied, the syntheses may yield a free base, a TFA salt or other salt forms which can be applied equally to further synthesis steps.

| Example | Structure | Diamine applied | Synthesis comment |
|---------|-----------|-----------------|-------------------|
| III.2 | 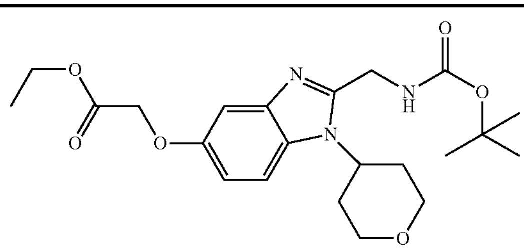 | V.2 | Purification by silica gel chromatograpy (cyclohexane-> ethyl acetate-> ethyl acetate/MeOH 95:5 |
| III.3 | 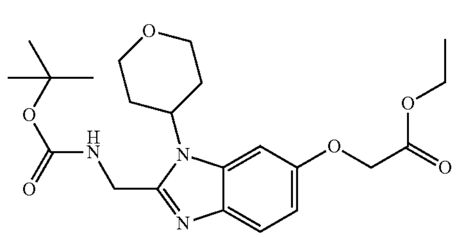 [SMILES: CCOC(=O)COc1ccc2nc(CNC(=O)OC(C)(C)C)n(C3CCOCC3)c2c1] | V.4 | Trituration with diethyl ether |

| Example | Structure | Amine applied | Aryl halide applied | Synthesis comment |
|---|---|---|---|---|
| IV.2 | 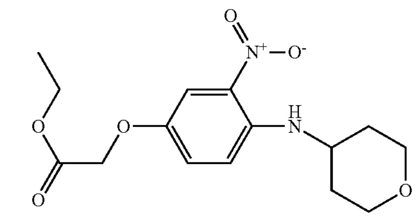 [SMILES: CCOC(=O)COc1ccc(NC2CCOCC2)c([N+](=O)[O-])c1] | | VII.3 | |
| IV.3 | 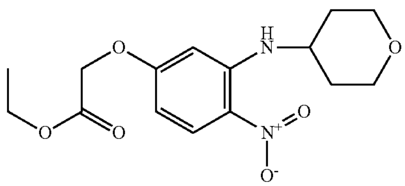 [SMILES: CCOC(=O)COc1ccc([N+](=O)[O-])c(NC2CCOCC2)c1] | | VII.2 | |
| IV.4 | 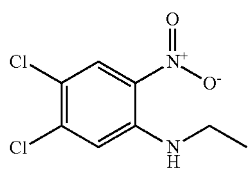 | | | Addition of K₂CO₃ (2.0 eq) |
| IV.5 | 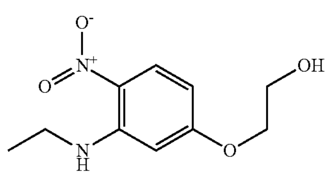 [SMILES: CCNc1cc(OCCO)ccc1[N+](=O)[O-]] | | VII.4 | 10 eq. of amine applied |
| IV.6 | 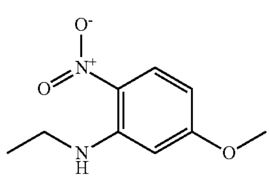 | | | 10 eq. of amine applied |
| IV.7 | 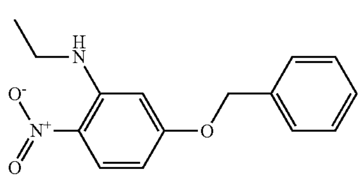 [SMILES: CCNc1cc(OCc2ccccc2)ccc1[N+](=O)[O-]] | | VII.5 | 3 eq. amine in THF without additional base; 1 h at 90° C. (microwave heating; closed vessel) |
| IV.8 | 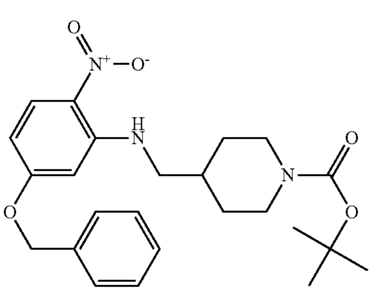 [SMILES: CC(C)(C)OC(=O)N1CCC(CNc2cc(OCc3ccccc3)ccc2[N+](=O)[O-])CC1] | | VII.5 | 1.5 eq. of triethyl-amine applied as base; 1 h at 90° C. in microwave oven |

Intermediate V.1

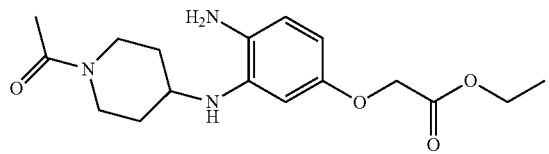

Intermediate IV.1 (11.8 g; 30.4 mmol) in ethanol (120 ml) is hydrogenated in a Parr apparatus (r.t., 50 psi hydrogen; catalyst: Pd/C 5%; 1.00 g) over night. The catalyst is filtered off under nitrogen and the filtrate is applied directly to the next reaction step as described there.

$C_{17}H_{25}N_3O_4$ ESI Mass spectrum: m/z=336 [M+H]+

The following intermediates are prepared accordingly from the respective starting materials as indicated. Due to conditions applied, the syntheses may yield a free base, a TFA salt or other salt forms which can be applied equally to further synthesis steps.

| Example | Structure | Starting material applied | Synthesis comment |
|---|---|---|---|
| V.2 | 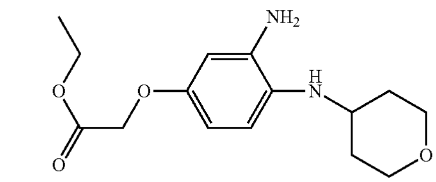 [SMILES: CCOC(=O)COc1ccc(NC2CCOCC2)c(N)c1] | IV.2 | |
| V.3 | 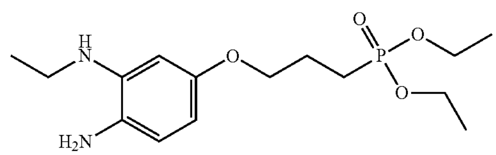 [SMILES: CCNc1cc(OCCCP(=O)(OCC)OCC)ccc1N] | VIII.1 | |
| V.4 | 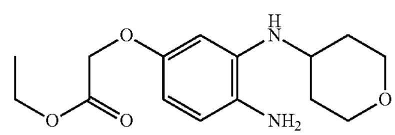 [SMILES: CCOC(=O)COc1ccc(N)c(NC2CCOCC2)c1] | IV.3 | |
| V.5 | 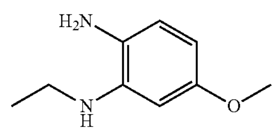 | IV.6 | Solvent is methanol |
| V.6 | 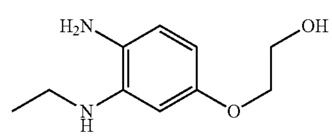 | IV.5 | |
| V.7 | 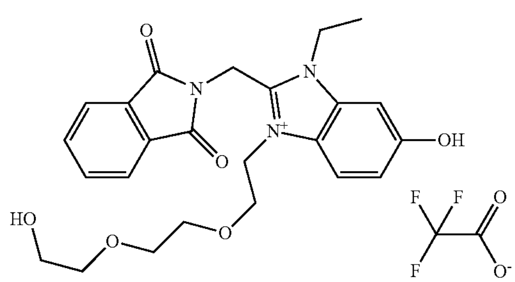 [SMILES: CCn1c(CN2C(=O)c3ccccc3C2=O)[n+](CCOCCOCCO)c2ccc(O)cc21 ; O=C([O-])C(F)(F)F] | IX.1 | Solvent is methanol |
| V.8 | 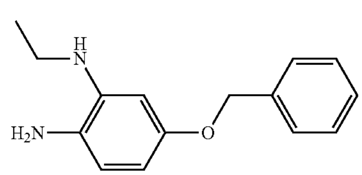 [SMILES: CCNc1cc(OCc2ccccc2)ccc1N] | IV.7 | Catalyst: Raney-Nickel; solvent: THF |

-continued

| Example | Structure | Starting material applied | Synthesis comment |
|---------|-----------|---------------------------|-------------------|
| V.9 | 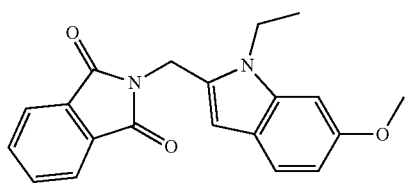 | IV.8 | Solvent is THF |

Intermediate VI.1

VI.1

A mixture of the diaminobenzene intermediate V.5 (THF solution; theory: 15.6 g; 94.0 mmol), N-phthaloylglycine (19.3 g; 94.03 mmol), TBTU (33.2 g; 103 mmol) and TEA (14.3 ml; 103 mmol) is stirred at r.t. for 3 h. The precipitate is filtered off, dried, and taken up in glacial acetic acid and refluxed for 2 h. The mixture is evaporated. The residue is taken up in water and extracted with ethyl acetate. The organic layer is separated, dried and evaporated. The residue is refluxed in ethyl acetate, cooled to r.t., filtered off, washed with ethyl acetate and dried.

$C_{19}H_{17}N_3O_3$ ESI Mass spectrum: m/z=336 [M+H]+

The following intermediates are prepared accordingly from the respective diaminobenzenes as indicated. Due to conditions applied, the syntheses may yield a free base, a TFA salt or other salt forms which can be applied equally to further synthesis steps.

| Example | Structure | Diaminobenzene applied | Synthesis comment |
|---------|-----------|------------------------|-------------------|
| VI.2 | 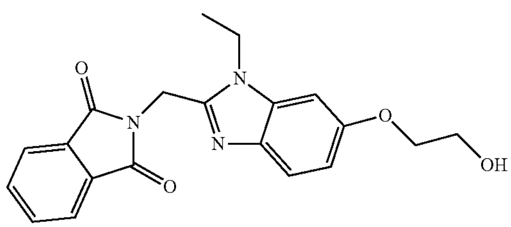 [SMILES: CCn1c(CN2C(=O)c3ccccc3C2=O)nc2ccc(OCCO)cc21] | V.6 | |
| VI.3 | 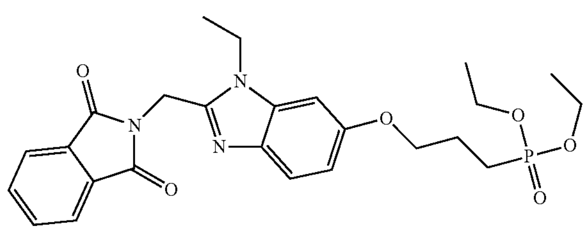 [SMILES: CCOP(=O)(CCCOc1ccc2nc(CN3C(=O)c4ccccc4C3=O)n(CC)c2c1)OCC] | V.3 | |
| VI.4 | 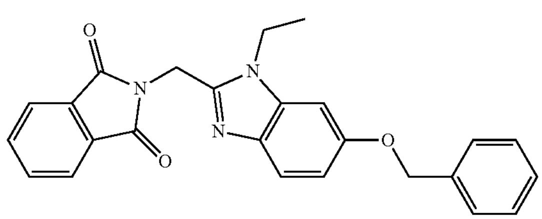 [SMILES: CCn1c(CN2C(=O)c3ccccc3C2=O)nc2ccc(OCc3ccccc3)cc21] | V.8 | |

| Example | Structure | Diaminobenzene applied | Synthesis comment |
|---------|-----------|------------------------|-------------------|
| VI.5 | 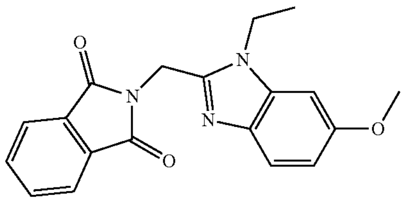 [SMILES: CCn1c(CN2C(=O)c3ccccc3C2=O)nc2ccc(OC)cc21] | V.5 | |
| VI.6 | 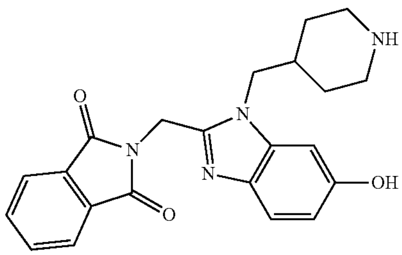 [SMILES: O=C1c2ccccc2C(=O)N1Cc1nc2ccc(O)cc2n1CC1CCNCC1] | V.9 | Purification by by RP-HPLC (column: SunFire C18; water-ACN; modifier TFA) |

Intermediate VII.1

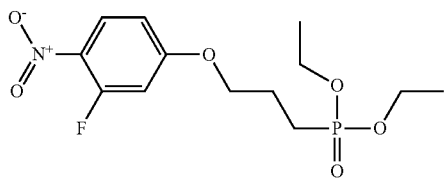

VII.1

A mixture of 3-fluoro-4-nitrophenol (2.56 g; 16.30 mmol), diethyl (3-bromopropyl)-phosphonate (3.26 ml; 16.98 mmol) and potassium carbonate (2.48 g; 17.9 mmol) in ACN (20 ml) is stirred for 4 h at 80° C. After cooling to r.t. the insoluble material is filtered off and discarded. The mother liquor is evaporated.

$C_{13}H_{19}FNO_6P$ ESI Mass spectrum: m/z=336 [M+H]+

The following intermediates are prepared accordingly from the respective nitrophenols and alkyl halides as indicated. Due to conditions applied, the syntheses may yield a free base, a TFA salt or other salt forms which can be applied equally to further synthesis steps.

| Example | Structure | Nitrophenol applied | Alkyl halide applied | Synthesis comment |
|---------|-----------|---------------------|----------------------|-------------------|
| VII.2 | 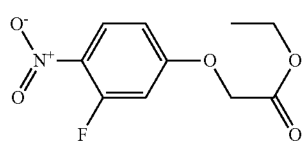 [SMILES: CCOC(=O)COc1ccc([N+](=O)[O-])c(F)c1] | | | Solvent is DMF; purification by extraction with water |
| VII.3 | 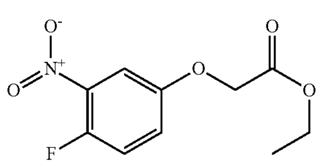 [SMILES: CCOC(=O)COc1ccc(F)c([N+](=O)[O-])c1] | | | Solvent is DMF; purification by extraction with water |
| VII.4 | 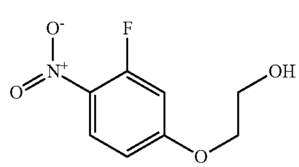 [SMILES: O=[N+]([O-])c1ccc(OCCO)cc1F] | | | Solvent is acetone: purification by silica gel chromatography (petrol ether/ethyl acetate:15%-> 50%) |

| Example | Structure | Nitrophenol applied | Alkyl halide applied | Synthesis comment |
|---|---|---|---|---|
| VII.5 | 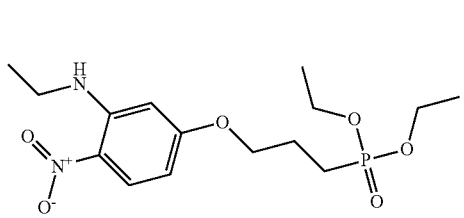 | OH, O⁻, N⁺=O, F (4-nitro-3-fluorophenol) | Br-CH₂-Ph (benzyl bromide) | |

Intermediate VIII.1

VIII.1

[structure of intermediate VIII.1]

A mixture of intermediate VII.1 (23.58 g; 63.30 mmol) and ethyl amine (2 M in THF; 80.0 ml; 160 mmol) is stirred at 90° C. for 1 h (microwave heating). The mixture is diluted with ethyl acetate and washed with water. The organic layer is separated, dried and evaporated.

$C_{15}H_{25}N_2O_6P$ ESI Mass spectrum: m/z=361 [M+H]+

HPLC analytics: RT=0.69 min (HPLC method 1)

Intermediate IX.1

IX.1

[structure of intermediate IX.1]

A mixture of intermediate VI.4 (1.50 g; 3.65 mmol) and 2-[2-(2-iodoethoxy)ethoxy]ethan-1-ol (prepared from 2-[2-(2-chloroethoxy)ethoxy]ethan-1-ol by Finkelstein exchange with sodium iodide; 3.79 g; 14.6 mmol) in ACN (15 ml) is stirred at 120° C. for 7 h (closed vessel). The mixture is evaporated and the residue is purified by RP-HPLC (column: SunFire C18; water-ACN; modifier TFA) to yield the title compound.

$C_{31}H_{34}N_3O_6 \times$ TFA ESI Mass spectrum: m/z=544 [M+]

HPLC analytics: RT=0.78 min (HPLC method 2)

The following intermediates are prepared accordingly from the respective alkyl halides and benzimidazoles as indicated. Due to conditions applied, the syntheses may yield a TFA salt or other salt forms which can be applied equally to further synthesis steps.

| Example | Structure | Alkyl halide applied | Benzimidazole applied | Synthesis comment |
|---|---|---|---|---|
| IX.2 | 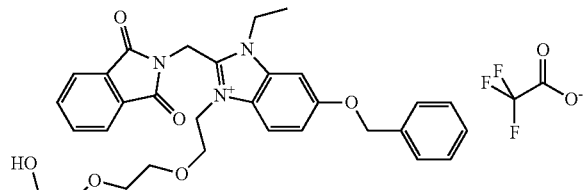 | 3-Iodopropene | VI.3 | |
| IX.3 | [structure] | Iodoethane | XXVII.4 | Reaction over night |

Intermediate X.1

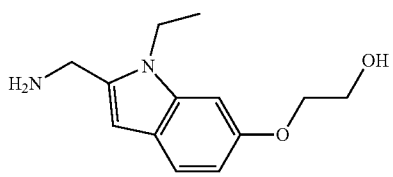

X.1

A mixture of intermediate VI.2 (310 mg; 0.848 mmol) and hydrazine hydrate (0.20 mL; 4.12 mmol) in ethanol (10 mL) refluxed for 1 h. After cooling to r.t. precipitates are filtered off. The mother liquor is evaporated and the residue is taken up in DCM. Insolubles are filtered off and discarded. The mother liquor is evaporated and the crude product is further reacted without chromatographic purification.

$C_{12}H_{17}N_3O_2$ ESI Mass spectrum: m/z=236 [M+]

The following intermediates are prepared accordingly from the respective protected amines as indicated. Due to conditions applied, the syntheses may yield a free base, a TFA salt or other salt forms which can be applied equally to further synthesis steps.

| Example | Structure | Protected amine applied | Sythesis comment |
|---|---|---|---|
| X.2 | 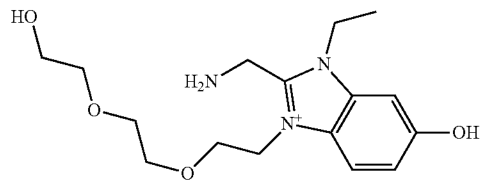 [SMILES: CCn1c(CN)[n+](CCOCCOCCO)c2ccc(O)cc21] | V.7 | Reaction at 60° C. over night |
| X.3 | 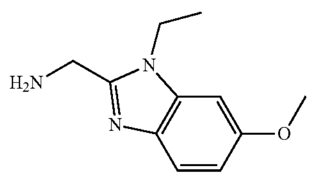 | VI.5 | |
| X.4 | 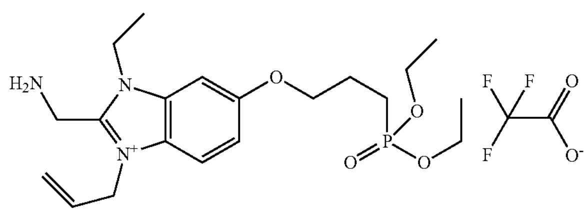 [SMILES: C=CC[n+]1c(CN)n(CC)c2cc(OCCCP(=O)(OCC)OCC)ccc21 ; O=C([O-])C(F)(F)F] | IX.2 | |
| X.7 | 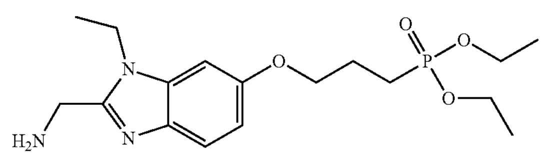 [SMILES: CCOP(=O)(CCCOc1ccc2nc(CN)n(CC)c2c1)OCC] | VI.3 | |
| X.8 | 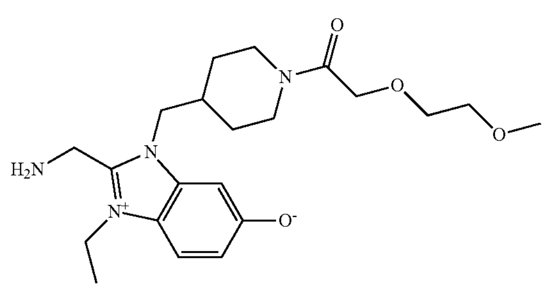 [SMILES: CC[n+]1c(CN)n(CC2CCN(C(=O)COCCOC)CC2)c2cc([O-])ccc21] | IX.3 | Reaction at 60° C. over night |

Intermediate XI.1

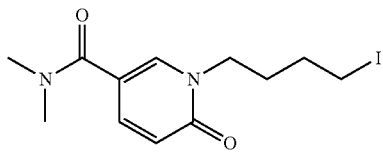
XI.1

A mixture of 1,4-diiodobutane (3.97 ml; 30.1 mmol, cesium carbonate (1.96 g; 6.02 mmol), DMF (10 ml) and intermediate XII.1 (1.00 g; 3.09 mmol) is stirred at 70° C. over night. Potassium tert-butylate (338 mg; 3.09 mmol) is added and the mixture is stirred for further 2 h at 70° C. Water is added and the mixture is extracted with DCM. The organic layer is dried (MgSO$_4$) and evaporated. The product is purified by RP-HPLC (column: SunFire C18; water-ACN; modifier TFA) to yield the title compound.

$C_{12}H_{17}IN_2O_2$ ESI Mass spectrum: m/z=349 [M+H]+

Intermediate XII.1

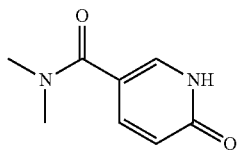
XII.1

A mixture of 6-hydroxynicotinic acid (4.3 g; 30.9 mmol) and thionyl chloride (4.5 ml; 61.7 mmol) is refluxed for 2 h. Volatiles are evaporated and the residue is codestilled with toluene. To the residue is added dimethylamine (2 mol/L in THF; 30.9 ml; 61.8 mmol) while cooling with an ice-bath, then the mixture is stirred at r.t. over night. Volatiles are evaporated and the crude product is further reacted without chromatographic purification.

$C_8H_{10}N_2O_2$ ESI Mass spectrum: m/z=165 [M−H]−

Intermediate XIII.1

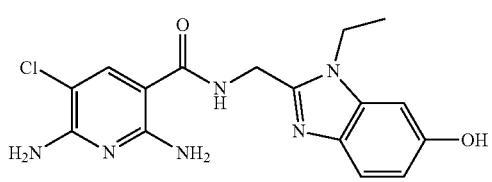
XIII.1

A mixture of intermediate XVIII.6 (1.60 g; 4.26 mmol), boron tribromide (1 mol/L in DCM; 21.3 ml; 21.3 mmol) and DCM (20 ml) is stirred at r.t. over night. Water is added and the complete mixture is evaporated. The residue is taken up in methanol, insolubles are filtered off and discarded, the filtrate is evaporated. The product is purified by RP-HPLC (modifier: TFA) to yield the title compound.

$C_{15}H_{16}ClN_7O_2$ ESI Mass spectrum: m/z=360 [M−H]−

Intermediate XIV.1

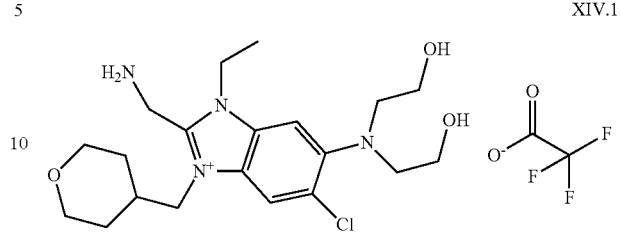
XIV.1

A mixture of intermediate XV.1 (168 mg; 0.269 mmol), TFA (2.0 ml) and DCM (5.0 ml) is stirred at r.t. for 1 h. Volatiles are evaporated and the residue is taken up in methanol and ammonia (32% aq. solution; 2.0 ml). The mixture is stirred for 1 h at r.t., then volatiles are evaporated and the residue is purified by RP-HPLC (modifier: TFA) to yield the title compound.

$C_{20}H_{32}ClN_4O_3 \times C_2F_3O_2$ ESI Mass spectrum: m/z=411 [M]+

Intermediate XV.1

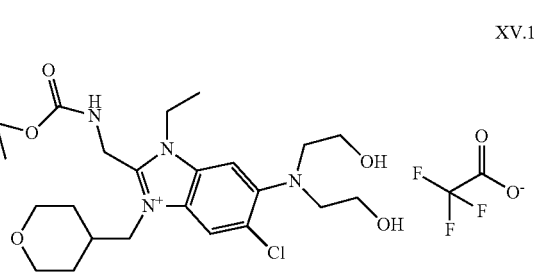
XV.1

A mixture of intermediate XIX.1 (500 mg; 1.21 mmol) and 4-iodomethyl-tetrahydropyrane (1.07 g; 4.73 mmol) in ACN (5.0 ml) is heated to 120° C. (microwave heating; closed vessel) for 7 h. Additional 4-iodomethyl-tetrahydropyran (1.07 g; 4.73 mmol) is added and the mixture is again heated to 120° C. (microwave heating; closed vessel) over night. Volatiles are evaporated and the crude product is purified by RP-HPLC (modifier: TFA) to yield the title compound.

$C_{25}H_{40}ClN_4O_5 \times C_2F_3O_2$ ESI Mass spectrum: m/z=511 [M]+

Intermediate XVI.1

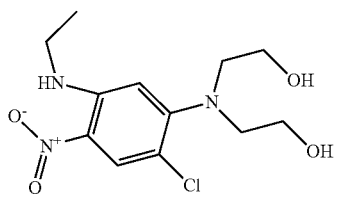
XVI.1

A mixture of intermediate IV.4 (5.00 g; 21.3 mmol), diethanolamine (2.3 ml; 24.1 mmol), potassium tert-butylate (5.01 g; 44.7 mmol) and DMF (50 ml) is stirred at r.t. for 2 h. Water is added, the mixture is evaporated and the residue is purified by silica gel chromatography (DCM/methanol 2%→6%) to yield the title compound.

$C_{12}H_{18}ClN_3O_4$ ESI Mass spectrum: m/z=304 [M+H]+

Intermediate XVII.1

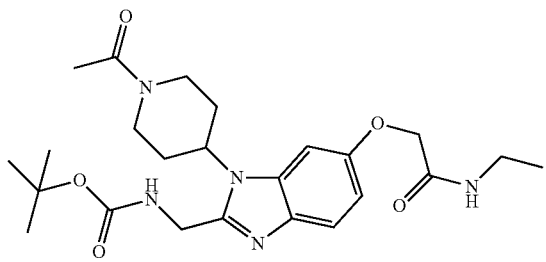

A mixture of the acid intermediate II.1 (1.47 g; 2.47 mmol), TBTU (1.03 g; 3.21 mmol) and N-methylmorpholine (0.92 ml; 8.40 mmol) in DMF (40 ml) is stirred at r.t. for 1 h. Ethylamine hydrochloride (221 mg; 2.72 mmol) is added. After stirring for 2 h the mixture is evaporated. The residue is taken up in ethyl acetate and washed with water and $NaHCO_3$ (sat. aq. solution). The organic layer is separated, dried and evaporated to yield the crude title compound which is further reacted without chromatographic purification.

$C_{24}H_{35}N_5O_5$ ESI Mass spectrum: m/z=474 [M+H]+

The following intermediates are prepared accordingly from the respective amines and acids as indicated. Due to conditions applied, the syntheses may yield a free base, a TFA salt or other salt forms which can be applied equally to further synthesis steps.

| Example | Structure | Amine applied | Acid applied |
|---------|-----------|---------------|--------------|
| XVII.2 | 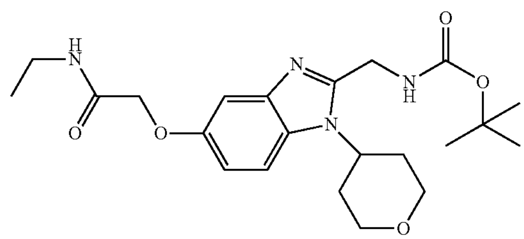 [SMILES: CCNC(=O)COc1ccc2c(c1)nc(CNC(=O)OC(C)(C)C)n2C1CCOCC1] | ClH H₂N— | II.2 |
| XVII.3 | 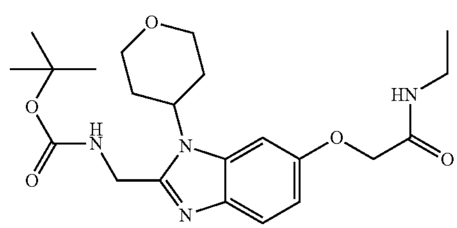 [SMILES: CCNC(=O)COc1ccc2nc(CNC(=O)OC(C)(C)C)n(C3CCOCC3)c2c1] | ClH H₂N— | II.3 |
| XVII.4 | 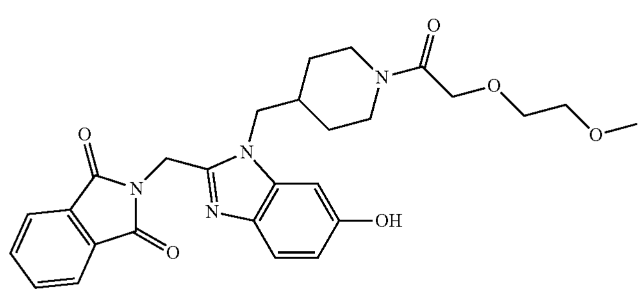 [SMILES: COCCOCC(=O)N1CCC(Cn2c(CN3C(=O)c4ccccc4C3=O)nc3ccc(O)cc32)CC1] | VI.6 | 2-(2-methoxy-ethoxy)-acetic acid |

Intermediate XVIII.1

XXIV.1

A mixture of Intermediate X.7 (2.75 g; 7.44 mmol), Intermediate A.1 (1.40 g; 7.44 mmol), HATU (2.92 g; 7.44 mmol) and TEA (2.09 ml; 14.9 mmol) in DMF (15 ml) is stirred at r.t. over night. The mixture is poured on ice water and the resulting precipitate is filtered off, washed with water and dried.

$C_{22}H_{31}ClN_7O_5P$ ESI Mass spectrum: m/z=540 [M+H]+
HPLC analytics: RT=0.68 min (HPLC method 2)

The following intermediates of general formula XVIII.A are prepared accordingly from the respective amines as indicated. Due to conditions applied, the syntheses may yield a free base, a TFA salt or other salt forms which can be applied equally to further synthesis steps.

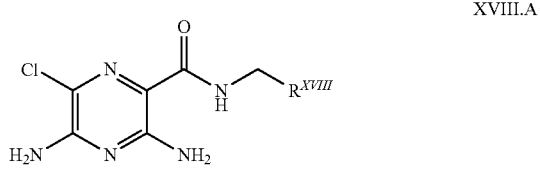

XVIII.A

| Example | $R^{XVIII}$ | Amine applied | Synthesis comment |
|---|---|---|---|
| XVIII.2 | | I.1 | Coupling reagent: TBTU; base: N-methylmorpholine; Purification by RP-HPLC (modifier: TFA) |
| XVIII.3 | | I.2 | Coupling reagent: TBTU; base: N-methylmorpholine; Purification by RP-HPLC (modifier: TFA) |
| XVIII.4 | | I.3 | Coupling reagent: TBTU; base: N-methylmorpholine; Purification by RP-HPLC (modifier: TFA) |
| XVIII.5 | | X.1 | Coupling reagent: TBTU; purified by extraction with DCM |
| XVIII.6 | | X.3 | Mixture diluted with NaHCO₃ (sat. aq. solution) to achieve precipitation |

Intermediate XIX.1

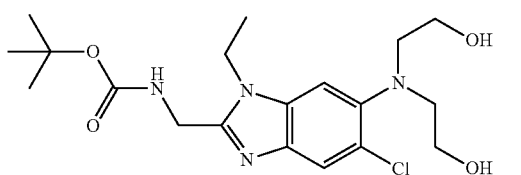

To a solution of intermediate XVI.1 (2.00 g; 6.59 mmol) and tert-butyl-N-(2-oxoethyl)-carbamate (1.10 g; 6.91 mmol) in ethanol (60 ml) is added dropwise a solution of sodium dithionite (6.00 g; 29.3 mmol) in water (40 ml). The mixture is stirred at 50° C. for 5 h, allowed to cool to r.t., alkalified by addition of sodium carbonate, and extracted with ethyl acetate. The organic layer is dried (sodium sulphate) and evaporated. The residue is purified by silica gel chromatography (DCM/methanol 3%→6%) to yield the title compound.

$C_{19}H_{29}ClN_4O_4$ ESI Mass spectrum: m/z=411 [M–H]–

Intermediate XX.1

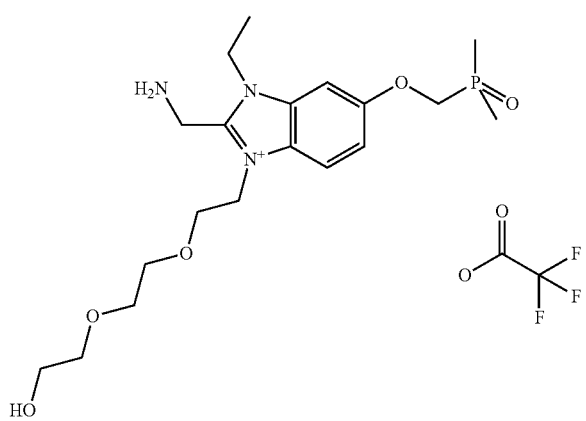

Stage 1:
A mixture of 3-fluoro-4-nitro-phenol (0.94 g; 5.96 mmol) and ethylamine (2M in THF; 10.00 mL; 20.00 mmol) is stirred at 90° C. for 1 hour in a microwave. The mixture is diluted with water and EtOAc. The organic layer is separated, dried and evaporated.
Yield: 0.63 g (58% of theory)
$C_8H_{10}N_2O_3$ ESI Mass spectrum: m/z=183 [M+H]+

Stage 2:
Intermediate XXXI.1 stage 1 (0.63 g; 3.46 mmol), potassium carbonate (0.53 g; 3.46 mmol), potassium iodide (0.57 g; 3.46 mmol) and chloromethyl(dimethyl)phosphine oxide (0.48 g; 3.80 mmol) in DMSO (10 mL) are stirred at 110° C. for 3 days. After cooling to r.t. the mixture is diluted with DCM. The organic layer is separated, dried and evaporated.
Yield: 0.81 g (86% of theory)
$C_{11}H_{17}N_2O_4P$ ESI Mass spectrum: m/z=273 [M+H]+

Stage 3:
Intermediate XXXI.1 stage 2 (0.81 g; 3.46 mmol) and Pd/C (10%; 0.16 g) in THF (10 mL) are hydrogenated in a Parr apparatus (50° C.; 3*10^5 Pa; 3 days). The catalyst is filtered off.
Yield: 0.72 g (100% of theory)
$C_{11}H_{19}N_2O_2P$ Stage 4:
A mixture of N-phthaloylglycine (7.00 g; 0.03 mol), TBTU (10.96 g; 0.03 mol) and TEA (9.59 mL; 0.07 mol) in the remaining THF is stirred at r.t. for 10 minutes. Intermediate XXXI.1 stage 3 (8.27 g; 0.03 mol) is added. After stirring for 5 hours the mixture is diluted with water and extracted with EtOAc. The organic layer is separated, dried and evaporated.
The residue is taken up in glacial acetic acid (130 mL) and stirred at 100° C. over night. The solvent is removed and the residue is taken up in aq. NaHCO3 and methyl isobutyl ketene. The organic layer is separated, dried and evaporated. The residue is purified by RP-HPLC (modifier: TFA).
Yield: 2.78 g (20% of theory)
$C_{21}H_{22}N_3O_4P$
ESI Mass spectrum: m/z=412 [M+H]+

Stage 5:
A mixture of intermediate XXXI.1 stage 4 (3.09 g; 7.51 mmol) and 2-[2-(2-iodoethoxyethoxy]ethanol (19.53 g; 75.11 mmol) and DIPEA (1.40 mL; 8.14 mmol) in ACN (30 mL) is stirred at 120° C. for 2 hours in a microwave and for further 48 hours at 120° C. The mixture is purified by RP-HPLC (modifier: TFA).
Yield: 2.70 g (11% of theory)
$C_{27}H_{35}N_3O_7P*C_2F_3O_2$
ESI Mass spectrum: m/z=261 [M+H]+

Stage 6:
A mixture of intermediate XXXI.1 stage 5 (2.70 g; 1.23 mmol) and hydrazine hydrate (2.00 mL; 41.15 mmol) in MeOH (20 mL) is stirred at 60° C. over night. After cooling to r.t. the resulting precipitate is filtered off and discarded. The solvent is evaporated. The residue is purified by RP-HPLC (modifier: TFA).
Yield: 0.66 g (100% of theory)
$C_{19}H_{33}N_3O_5P*C_2F_3O_2$ ESI Mass spectrum: m/z=414 [M+]

7.2 SYNTHESIS OF EXAMPLES

Example 1.1

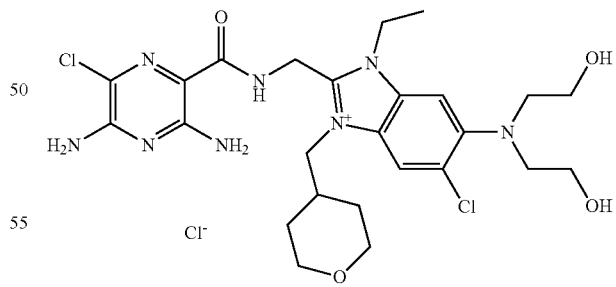

A mixture of 3,5-diamino-6-chloro-pyrazine-2-carboxylic acid (Intermediate A.1; 10 mg; 0.053 mmol), the amine intermediate XIV.1 (as a TFA salt; 22 mg; 0.042 mmol) the coupling reagent HATU (50 mg; 0.132 mmol) and DIPEA (100 μl; 0.59 mmol) in DMF (5 ml) is stirred at r.t. over night. The mixture is purified by RP-HPLC (column: SunFire C18; water-ACN; modifier TFA) to yield the title compound.
$C_{25}H_{35}Cl_2N_8O_4 \times Cl$ ESI Mass spectrum: m/z=581 [M]+
HPLC analytics: RT=0.66 min (HPLC method 2)

The following compounds of general formula 1.A are prepared accordingly applying the respective amines as indicated. Due to conditions applied, the procedures may yield a chloride salt, a TFA salt or bis-TFA salt, a zwitterion or other salt forms.

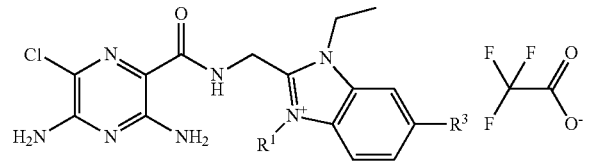

1.A

Example 2.1 is prepared analogously to the procedure described for the synthesis of example 1.2 from Intermediate A.2; 70 mg; 0.30 mmol) and the amine intermediate X.2 (0.162 g; 0.30 mmol).

$C_{21}H_{28}BrN_7O_5 \times C_2F_3O_2$ ESI Mass spectrum: m/z=538 $[M]^+$

HPLC analytics: RT=0.58 min (HPLC method 2)

The following compounds of general formula 2.A are prepared accordingly applying the respective amines as indicated. Due to conditions applied, the procedures may yield a

| Example | $R^1$ | $R^3$ | Amine applied | Synthesis comment | ESI mass spectrum | HPLC retention time (min) | HPLC method |
|---|---|---|---|---|---|---|---|
| 1.2 | ![HO-CH2CH2-O-CH2CH2-O-CH2CH2-*] | —OH | X.2 | | 494 (M)+ | 0.52 | 2 |
| 1.3 | ![*-CH2-CH=CH-CH2-*] | ![P(O)(OEt)(OCH2CH2CH2O*)] | X.4 | | 580 (M)+ | 0.72 | 2 |
| 1.4 | ![HO-CH2CH2-O-CH2CH2-O-CH2CH2-*] | ![dimethylphosphinoyl-CH2-O-*] | XX.1 | | 584 (M)+ | 0.34 | 13 |

Example 2.1

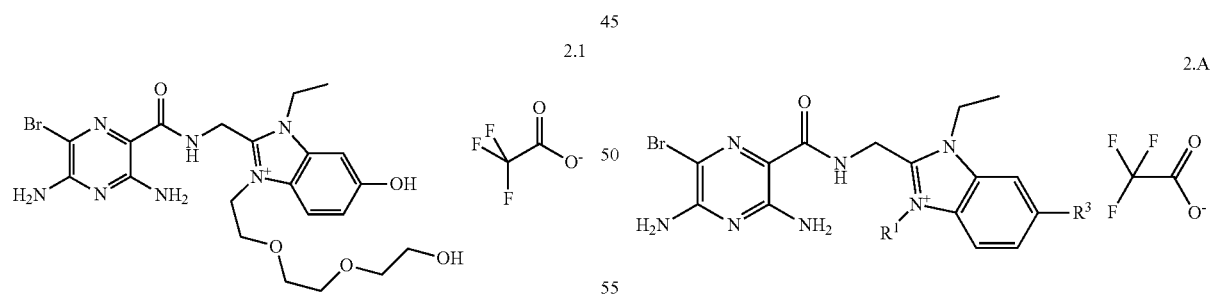

2.1 chloride salt, a TFA salt or bis-TFA salt, a zwitterion or other salt forms.

2.A

| Example | $R^1$ | $R^3$ | Amine applied | Synthesis comment | ESI mass spectrum | HPLC retention time (min) | HPLC method |
|---|---|---|---|---|---|---|---|
| 2.2 | ![*-CH2-CH=CH-CH2-*] | ![P(O)(OEt)(OCH2CH2CH2O*)] | X.4 | | 624 (M)+ | 0.72 | 2 |

Example 3.1

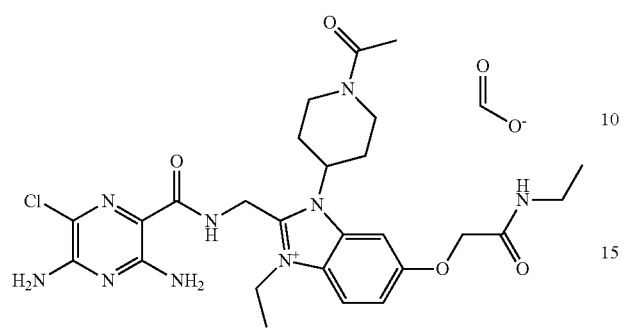

A mixture of Intermediate XVIII.2 (0.15 g; 0.248 mmol) and ethyl iodide (0.204 mL; 2.48 mmol) in ACN (4 ml) is stirred for 2 h at 120° C. (microwave heating, closed vessel). Further ethyl iodide (0.102 mL; 1.24 mmol) is added and the mixture is stirred for one further hour at 120° C. The mixture is purified by RP-HPLC (water-ACN; modifier ammonium formate) to yield the title compound.

$C_{26}H_{35}ClN_9O_4 \times HCO_2$ ESI Mass spectrum: m/z=572 [M+]

HPLC analytics: RT=3.27 min (HPLC method 5)

The following compounds of general formula 3.A are prepared accordingly using the respective alkyl halides and benzimidazoles as indicated. Due to conditions applied, the procedures may yield a chloride salt, a TFA salt or bis-TFA salt, a zwitterion or other salt forms.

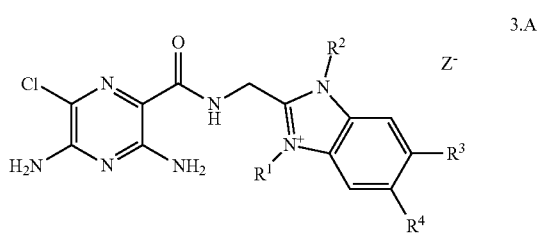

3.A

| Example | $R^1$ | $R^2$ | $R^3$ | $R^4$ | $Z^-$ | Alkyl halide applied | Benzimidazole applied | Synthesis comment: | ESI mass spectrum | HPLC retention time (min) | HPLC method |
|---|---|---|---|---|---|---|---|---|---|---|---|
| 3.2 | tetrahydropyranylmethyl* | *ethyl | H | | formate | ethyl iodide | XVIII.3 | | 531 (M)+ | 3.35 | 5 |
| 3.3 | tetrahydropyranylmethyl* | *ethyl | H | ether-acetamide* | formate | ethyl iodide | XVIII.4 | | 531 (M)+ | 3.33 | 5 |
| 3.4 | tetrahydropyranylmethyl* | *phosphonate chain | * | H | trifluoroacetate | tetrahydropyranylmethyl iodide | XVIII.1 | b | 534 (M)+ | 0.39 | 7 |
| 3.5 | cyanopropyl* | *phosphonate chain | * | H | trifluoroacetate | bromocyanobutyl | XVIII.1 | e | 579 (M)+ | 0.42 | 1 |

-continued

| Example | R¹ | R² | R³ | R⁴ | Z⁻ | Alkyl halide applied | Benzimidazole applied | Synthesis comment: | ESI mass spectrum | HPLC retention time (min) | HPLC method |
|---|---|---|---|---|---|---|---|---|---|---|---|
| 3.6 | (cyanopropyl) | (diethyl phosphonate ethyl) | | H | trifluoroacetate | Br(cyanopropyl) | XVIII.1 | a | 607 (M)⁺ | 0.7 | 2 |
| 3.7 | (pyridinone dimethylcarboxamide butyl) | (ethyl) | (hydroxypropyl) | H | trifluoroacetate | XI.1 | XXIV.5 | d | 626 (M)⁺ | 0.37 | 14 |
| 3.8 | (cyanopropyl) | (ethyl) | —OH | H | trifluoroacetate | Br(cyanopropyl) | XIII.1 | c | 429 (M)⁺ | 0.40 | 3 | a: Reaction time: 6 h at 120° C. 22 equivalents of 4-bromobutyronitrile applied. Purification by RP-HPLC (modifier: TFA).

b: Reaction time: 10 h at 120° C. Purification by RP-HPLC (modifier: TFA).

c: only 1 eq. of alkylating agent; 2 eq. of lithium bis(trimethylsilyl)amide added; Purification by RP-HPLC (modifier: TFA).

d: Purification by RP-HPLC (modifier: TFA).

e: Reaction time: 2 h and at 140° C. 22 equivalents of 4-bromobutyronitrile applied. Purification by RP-HPLC (modifier: TFA).

Example 4.1

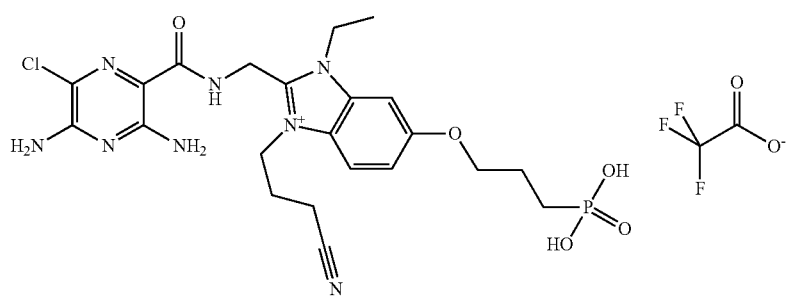

4.1

A mixture of Example 3.6 (153 mg; 0.212 mmol), bromotrimethylsilane (1.28 ml; 9.76 mmol) and triethylamine (0.50 ml; 3.56 mmol in THF (10 ml) is stirred at 80° C. for 4 h. The mixture is purified by RP-HPLC (column: SunFire C18; water-ACN; modifier TFA) to yield the title compound.

$C_{22}H_{28}ClN_8O_5P \times C_2F_3O_2$ ESI Mass spectrum: m/z=551 $[M]^+$

HPLC analytics: RT=0.58 min (HPLC method 2)

Example 5.1

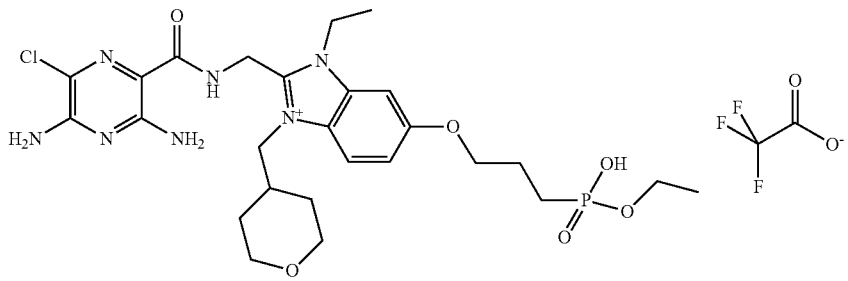

5.1

A mixture of example 3.4 (100.0 mg; 0.133 mmol), lithium bromide (115 mg; 1.33 mmol) and DMF (3.0 ml) is stirred at 110° C. (bath temperature) over night. Volatiles are evaporated and the residue is purified by RP-HPLC (column: SunFire C18; water-ACN; modifier TFA).

$C_{26}H_{38}ClN_7O_6P \times C_2F_3O_2$ ESI Mass spectrum: m/z=610 $[M]^+$

HPLC analytics: RT=0.35 min (HPLC method 7)

Example 6.1

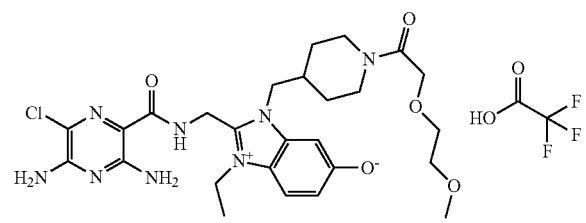

6.1

Example 6.1 is prepared analogously to the procedure described for the synthesis of example 1.1 from Intermediate A.1 (66 mg; 0.35 mmol) and the amine intermediate X.8 (0.140 g; 0.35 mmol).

$C_{26}H_{35}ClN_8O_5 \times C_2F_3O_2$ ESI Mass spectrum: m/z=575 $[M+H]^+$

HPLC analytics: RT=0.45 min (HPLC method 13)

8. ANALYTICAL METHODS AND PREPARATIVE CHROMATOGRAPHY

As a rule, $^1$H-NMR and mass spectra have been obtained for the compounds prepared. Mass peaks given (e.g. (M+H)+, (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for NH$_3$ relate to a concentrated solution of NH$_3$ in water. For silica gel chromatographic purifications, silica gel from Millipore (MATREX™, 35-70 my) is used.

Preparative Thin Layer Chromatography (TLC):

Preparative TLC plates from Merck (PLC Silica gel 60 $F_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to yield the purified compound.

Preparative HPLC:

Stationary phase: XBridge C18; 10 μm or SunFire C18; 10 μm (both from waters, www.waters.com)

Analytical HPLC/MS Methods

The HPLC retention times given are measured under the following parameters.

HPLC Method 1

| Column: SunFire C18, 2.1 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

HPLC Method 2

| Column: SunFire, 3 × 30 mm, 2.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method 3

| Column: XBridge BEH C18, 2.1 × 30 mm, 1.7 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

HPLC Method 4

| Column: SunFire C18, 4.6 × 30 mm, 3.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 98 | 2 | 2.5 | 60 |
| 1.50 | 0 | 100 | 2.5 | 60 |
| 1.80 | 0 | 100 | 2.5 | 60 |

HPLC Method 5
Column: Atlantis dC18 5 μm 4.6×50 mm, Temp 35° C.
Mobile phase: A=H2O 90%+10% CH3CN+CF3COOH 0.05%
B=CH3CN 90%+10% H2O

| Time in min | % A | % B | flow rate in ml/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

HPLC Method 6

| Column: SunFire C18, 4.6 × 30 mm, 3.5 μm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 98 | 2 | 2.5 | 60 |
| 1.50 | 0 | 100 | 2.5 | 60 |
| 1.80 | 0 | 100 | 2.5 | 60 |

HPLC Method 7

| Column: SunFire C18, 2.1 × 50 mm, 2.5 μm (Waters) | | | | |
|---|---|---|---|---|
| Gradient time [min] | % Sol [H2O, 0.1% TFA] | % Sol [ACN, 0.08% TFA] | Flow [ml/min] | Temp [° C.] |
| 0.00 | 95 | 5 | 1.5 | 60 |
| 0.75 | 0 | 100 | 1.5 | 60 |
| 0.85 | 0 | 100 | 1.5 | 60 |

HPLC Method 8
Column: Synergi Hydro RP100A, 2.5 μm, 3×50 mm
Mobile phase: A=H2O 90%+10% CH3CN+NH4COOH 5 mM
B=CH3CN 90%+H2O 10%

| Time in min: | % A | % B | Flow rate in mL/min |
|---|---|---|---|
| 0.00 | 100 | 0 | 1.2 |
| 4.00 | 0 | 100 | 1.2 |
| 5.30 | 0 | 100 | 1.2 |
| 5.50 | 100 | 0 | 1.2 |
| 6.00 | 100 | 0 | 1.2 |

HPLC Method 9
Column: BEH C18 1.7 μm 2.1×50 mm, Temp 35° C.
Mobile phase: A=H2O 90%+CH3CN 10%+NH4COOH 5 mM
B=CH3CN 90%+H2O 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

HPLC Method 10

| Column: XBridge C18, 3 × 30 mm, 2.5 μm (Waters) | | | | |
|---|---|---|---|---|
| Gradient/Solvent Time [min] | % Sol [H2O, 0.1% NH3] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method 11

| Column: XBridge C18, 4.6 × 30 mm, 2.5 μm (Waters) | | | | |
|---|---|---|---|---|
| Gradient/Solvent Time [min] | % Sol [H2O, 0.1% TFA] | % Sol [ACN] | Flow [ml/min] | Temp [° C.] |
| 0.00 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

HPLC Method 12

| Column: Sunfire C18_3.0 × 30 mm, 2.5 μm (Waters) | | | | |
|---|---|---|---|---|
| Gradient/Solvent Time [min] | % Sol [H2O 0.1% TFA] | % Sol [Acetonitrile] | Flow [ml/min] | Temp [° C.] |
| 0.0 | 98.0 | 1.0 | 2.0 | 60.0 |
| 0.9 | 0.0 | 100.0 | 2.0 | 60.0 |
| 1.1 | 0.0 | 100.0 | 2.0 | 60.0 |

HPLC Method 13

| Column: Sunfire C18_3.0 × 30 mm, 2.5 μm (Waters) | | | | |
|---|---|---|---|---|
| Gradient/Solvent Time [min] | % Sol [H2O 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

HPLC Method 14?

| Column: Sunfire C18, 4.6 × 30 mm, 2.5 μm (Waters) | | | | |
|---|---|---|---|---|
| Gradient/Solvent Time [min] | % Sol [H2O, 0.1% TFA] | % Sol [ACN] | Flow [ml/min] | Temp [° C.] |
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

The Following Abbreviations are Used Above and Hereinafter:
ACN Acetonitrile
BOC tert-Butoxycarbonyl
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
Eq. Molar equivalent
ESI Electrospray ionization
h hour
HATU O-(7-Azabenzotriazol-1-yl)-N,N,N',N'-tetramethyluronium hexafluorophosphate
HCl Hydrochloric acid
KOH Potassium hydroxide
l liter
LiHMDS Lithium bis(trimethylsilyl)amide
M mol/l
Min minutes
Mp melting point
NaOH Sodium hydroxide
n.d. not determined
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluronium-tetrafluoroborate
TEA Triethylamine
TFA Trifluoroacetic acid
THF Tetrahydrofurane
TLC Thin Layer Chromatography
TMS Trimethylsilyl

arrow and asterisk indicate the binding site, i.e. the point of attachment (here: atom "A") within a chemical entity (here exemplified by the group "A-R")

9. PHARMACOLOGICAL TEST METHOD

Ussing Chamber:

Mouse kidney M-1 cells were cultivated in DMEM containing 5% FCS and 5 μM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package Lab View for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as $IC_{50}$.

With the example compounds given above, the following $IC_{50}$ values were determined in the Ussing Chamber assay:

| Example | 1.1 | 1.2 | 1.3 | 1.4 | 2.1 | 2.2 | 3.1 | 3.2 | 3.3 | 3.4 | 3.5 | 3.6 | 3.7 | 3.8 | 3.8 | 4.1 | 5.1 | 6.1 |
|---|---|---|---|---|---|---|---|---|---|---|---|---|---|---|---|---|---|---|
| $IC_{50}$ [nM] | 13 | 1 | 1 | 13 | 1 | 2 | 10 | 2 | 1 | 2 | 19 | 5 | 13 | 11 | 11 | 31 | 8 | 3 |

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2\times10^5$ cells/1 $cm^2$ area) are seeded on filter inserts (Costar transwell polycarbonate filters, 0.4 μm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO4, 1.8 mM CaCl2, 4.17 mM NaHCO3, 1.19 mM Na2HPO4×7H2O, 0.41 mM NaH2PO4×H2O, 15 mM HEPES, 20 mM glucose, 0.25% BSA, pH 7.4) to prepare the transport solutions (10 μM compound, final DMSO<=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenished by HTP-4 buffer. The compound concentration in the samples is measured by HPLC-MS/MS or scintillation counting. The permeability coefficient (Papp) and efflux ratio are calculated according to:

Papp [cm/s]=(concentration receiver [nM]*volume receiver [mL]/time interval [sec])*(1/filter area)* (1/donor concentration [nM])

With example compounds given above, the following permeability values were determined in the CALU-3 cells assay:

| Example | 1.2 | 1.4 | 2.1 | 3.2 | 3.5 | 3.6 | 3.7 |
|---|---|---|---|---|---|---|---|
| Papp, AB [$10^{-6}$ cm/s] | 0.5 | 0.4 | 1.3 | <0.5 | 0.5 | 0.1 | 0.6 |
| Papp, BA [$10^{-6}$ cm/s] | 0.3 | 0.1 | 0.2 | 0.2 | 0.1 | 0.4 | 0.05 |

10. INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. COMBINATIONS

The compounds of formula (I) may be used on their own or in conjunction with other active substances of (I) according to the invention. If desired the compounds of formula (I) may also be used in combination with other pharmacologically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

12. FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

| Capsule for powder inhalation | |
|---|---|
| 1 capsule contains: | |
| active substance | 0.5 mg |
| lactose for inhalation | 5.0 mg |
| | 5.5 mg |
| Preparation: | |
| The active substance is mixed with lactose for inhalation. | |
| The mixture is packed into capsules in a capsule-making | |
| machine (weight of the empty capsule approx. 50 mg). | |
| weight of capsule: | 55.5 mg |

The invention claimed is:
1. A compound of formula (I),

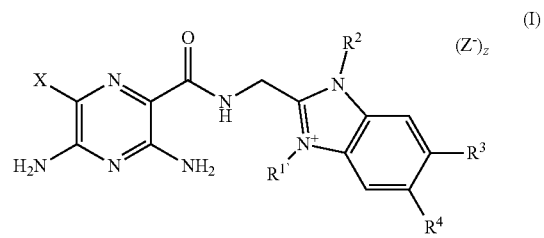

characterized in that
X denotes Cl or Br,
$R^1$ denotes allyl-, NC—$C_{3-4}$-alkylene-, H—(O—$CH_2$—$CH_2$)$_q$—, $CH_3$—(O—$CH_2$—$CH_2$)$_m$—, tetrahydropyranyl-($CH_2$)$_r$—, N—[$R^{11}$—(O—$CH_2$—$CH_2$)$_s$—$CH_2$—C(O)]-piperidin-4-yl-($CH_2$)$_r$— or $R^9R^{10}$N—C(O)-(2-oxo-2H-pyridin-1-yl)-$C_{3-5}$-alkylene-,
$R^2$ denotes $C_{1-3}$-alkyl-,
$R^3$ and $R^4$ denote independently H, halogen, HO—, (HO—$C_{2-3}$-alkylene)$_2$N—, ($R^7$O—)($R^8$O—)P(O)—($CH_2$)$_n$—O—, $R^5R^6$N—C(O)—$CH_2$—O—, HO—($CH_2$)$_2$—O—, ($CH_3$)$_2$P(O)—$CH_2$O— or a substituent of formula (bg)

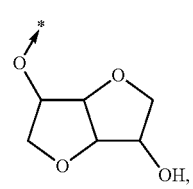

(bg)

and if $R^3$ denotes H or halogen, then $R^4$ does not denote H or halogen,
and if $R^4$ denotes H or halogen, then $R^3$ does not denote H or halogen,
$R^5$ and $R^6$ denote independently H or $C_{1-2}$-alkyl-, or
$R^5$ and $R^6$ together with the nitrogen atom they are attached to form a 6-membered heterocycle from the group consisting of thiomorpholine, thiomorpholine-S-oxide, thiomorpholine-dioxide,
$R^7$ and $R^8$ denote independently H or $C_{1-3}$-alkyl-,
$R^9$ and $R^{10}$ denote independently H or $C_{1-3}$-alkyl-,
$R^{11}$ denotes H or $C_{1-3}$-alkyl-,
m denotes 2, 3 or 4,
n denotes 2 or 3,
q denotes 3 or 4,
r denotes 0, 1, 2 or 3,
s denotes 0, 1 or 2, Z⁻ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate and p-toluenesulfonate, z denotes 0 for negatively charged substituents $R^1$-$R^4$, 1 for uncharged substituents $R^1$-$R^4$ or 2 for positively charged substituents $R^1$-$R^4$, wherein the asterisk (*) represents point of attachment to the remainder of the molecule and tautomers and optionally the pharmacologically acceptable acid addition salts thereof.

2. The compound of formula (I) according to claim 1, characterized in that $R^1$ denotes allyl-, NC—$C_{3-4}$-alkylene-, H—(O—$CH_2$—$CH_2$)$_q$—, tetrahydropyranyl-($CH_2$)$_{0-1}$—, N-acetyl-piperidinyl-, or $R^9R^{10}N$—C(O)-(2-oxo-2H-pyrid-1-yl)-$C_{3-5}$-alkylene-, $R^9$ and $R^{10}$ denote independently H or methyl-, q denotes 3 or 4.

3. The compound of formula (I) according to claim 1, characterized in that $R^3$ denotes H, HO—, (HO—$C_{2-3}$-alkylene)$_2$N—, ($R^7O$—)($R^8O$—)P(O)—($CH_2$)$_n$—O—, $R^5R^6N$—C(O)—$CH_2$—O— or HO—($CH_2$)$_2$—O—, and if $R^3$ denotes H, then $R^4$ does not denote H or halogen, $R^5$ and $R^6$ denote independently H or $C_{1-2}$-alkyl-, $R^7$ and $R^8$ denote independently H or $C_{1-3}$-alkyl-, n denotes 2 or 3.

4. The compound of formula (I) according to claim 1, characterized in that $R^4$ denotes H, halogen or $R^5R^6N$—C(O)—$CH_2$—O—, and if $R^4$ denotes H or halogen, then $R^3$ does not denote H, $R^5$, $R^6$ denote independently H or $C_{1-2}$-alkyl-.

5. The compound of formula (I) according to claim 1, characterized in that $R^1$ denotes a substituent selected from the group consisting of formula (aa)-(ag)

(aa)

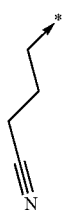

(ab)

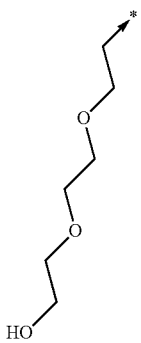

(ac)

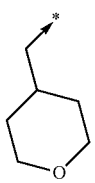

(ad)

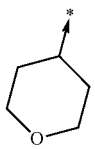

(ae)

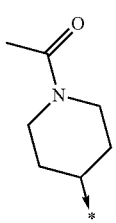

(af)

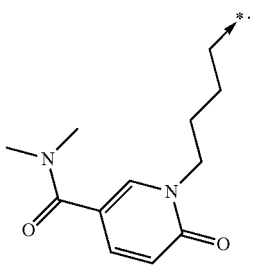

(ag)

6. The compound of formula (I) according to claim 1, characterized in that $R^2$ denotes ethyl-.

7. The compound of formula (I) according to claim 1, characterized in that $R^3$ denotes H, HO— or $R^3$ denotes a substituent selected from the group consisting of formula (ba)-(bf)

(ba) 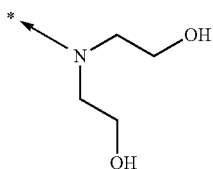

(bb) 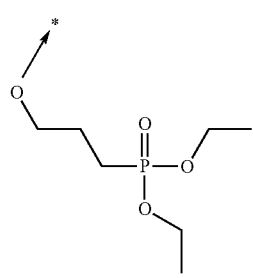

(bc) 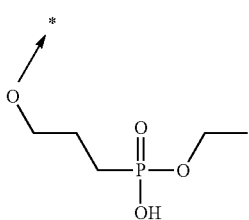

(bd) 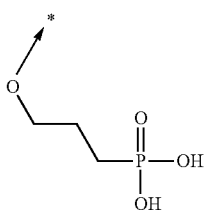

(be) 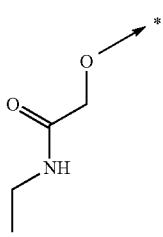

(bf) 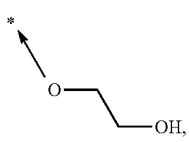

and if $R^3$ denotes H, then $R^4$ does not denote H or Cl.

8. The compound of formula (I) according to claim 1, characterized in that
$R^4$ denotes H, Cl or a substituent of formula (ca)

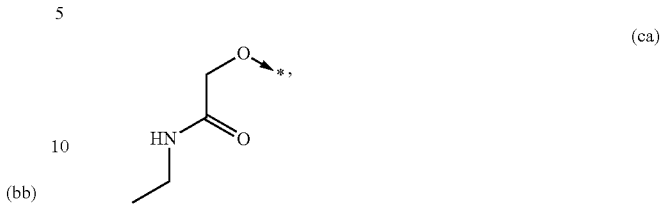

(ca)

and if $R^4$ denotes H or Cl, then $R^3$ does not denote H.

9. The compound of formula (I) according to claim 1, characterized in that
X denotes Cl or Br,
$R^1$ denotes a substituent selected from the group consisting of formula (aa)-(ag)

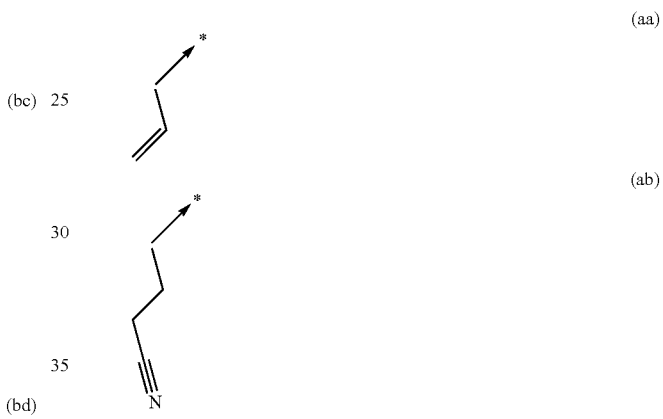

(aa)

(ab)

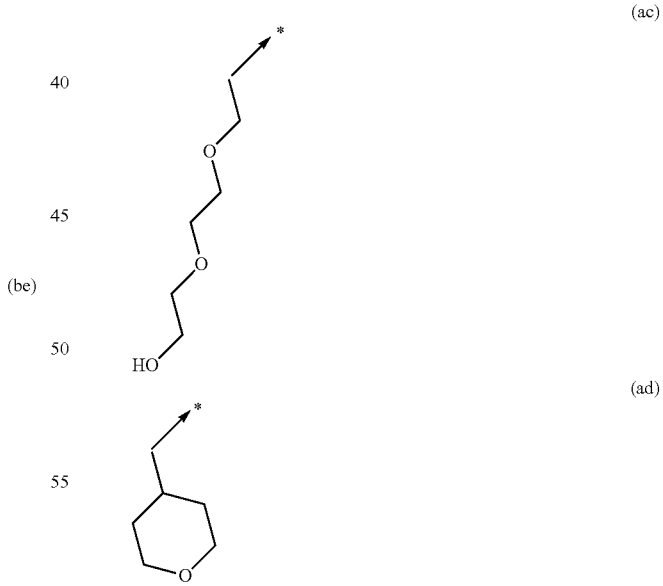

(ac)

(ad)

(ae)

-continued (af)

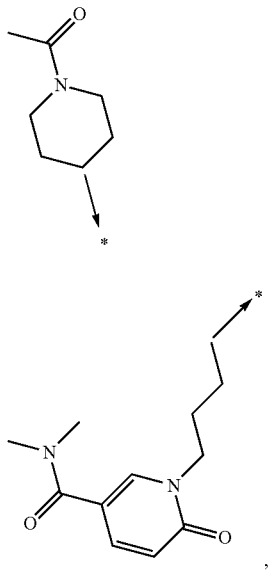

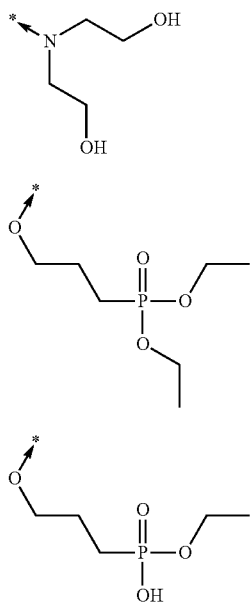

R² denotes ethyl-,
R³ denotes H, HO— or
R³ denotes a substituent selected from the group consisting of formula (ba)-(bf)

(ba)

*–N(CH₂CH₂OH)₂

(bb)

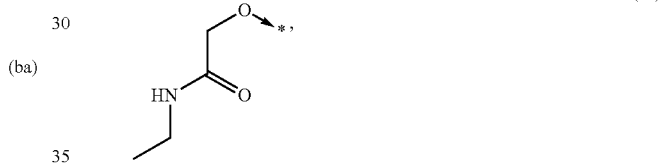

(bc)

-continued (bd)

(be)

(bf)

and if R³ denotes H, then R⁴ does not denote H or Cl,
R⁴ denotes H, Cl or a substituent of formula (ca)

(ca)

and if R⁴ denotes H or Cl, then R³ does not denote H,

Z⁻ denotes a physiologically acceptable anion selected from the group consisting of chloride, bromide, iodide, hydroxide, hydrogensulfate, sulfate, nitrate, phosphate, formiate, acetate, trifluoroacetate, fumarate, citrate, tartrate, oxalate, succinate, mandelate, methanesulfonate and p-toluenesulfonate, z denotes 0 for negatively charged substituents R¹-R⁴, 1 for uncharged substituents R¹-R⁴ or 2 for positively charged substituents R¹-R⁴, and tautomers and optionally the pharmacologically acceptable acid addition salts thereof.

10. A pharmaceutical composition comprising at least one compound according to claim 1 or a pharmaceutically acceptable salt thereof and a pharmaceutically acceptable carrier.

* * * * *